(12) United States Patent
Hoffmann et al.

(10) Patent No.: US 10,722,059 B2
(45) Date of Patent: Jul. 28, 2020

(54) SYSTEM FOR MONITORING THE LIQUID INTAKE OF A USER AND METHOD OF OPERATING THE SYSTEM

(71) Applicant: BELENUS Verwaltungsgesellschaft mbH, Munich (DE)

(72) Inventors: Bernd Hoffmann, Munich (DE); Susann Heinicke, Munich (DE)

(73) Assignee: BELENUS Verwaltungsgesellschaft mBH, Munich (DE)

( * ) Notice: Subject to any disclaimer, the term of this patent is extended or adjusted under 35 U.S.C. 154(b) by 0 days.

(21) Appl. No.: 16/279,727

(22) Filed: Feb. 19, 2019

(65) Prior Publication Data

US 2019/0174939 A1 Jun. 13, 2019

Related U.S. Application Data

(63) Continuation of application No. PCT/EP2017/070794, filed on Aug. 16, 2017.

(30) Foreign Application Priority Data

Aug. 19, 2016 (DE) .................. 10 2016 215 615

(51) Int. Cl.
| | |
|---|---|
| A47G 23/16 | (2006.01) |
| A61B 5/00 | (2006.01) |
| A61B 5/024 | (2006.01) |
| A47G 19/22 | (2006.01) |

(Continued)

(52) U.S. Cl.
CPC .............. *A47G 23/16* (2013.01); *A47G 19/00* (2013.01); *A47G 19/2227* (2013.01); *A47G 23/00* (2013.01); *A61B 5/02438* (2013.01); *A61B 5/4266* (2013.01); *A61B 5/4833* (2013.01); *A61B 5/4875* (2013.01); *A61B 5/74* (2013.01); *A61B 5/021* (2013.01)

(58) Field of Classification Search
None
See application file for complete search history.

(56) References Cited

U.S. PATENT DOCUMENTS

9,801,482 B1 * 10/2017 Alexander .......... A47G 19/2288
10,188,230 B2 * 1/2019 Hambrock .......... A47G 19/2227
(Continued)

FOREIGN PATENT DOCUMENTS

| DE | 102004004328 A1 | 8/2005 |
|---|---|---|
| EP | 2472488 A1 | 7/2012 |
| GB | 2435465 A | 8/2007 |

OTHER PUBLICATIONS

Hopper, Henry, "A Dozen Ways to Measure Fluid Level and How They Work | Sensors Magazine", URL: https://www.sensorsmag.com/components/a-dozen-ways-to-measure-fluid-level-and-how-they-work; Dec. 1, 2004; (retrieved Jan. 23, 2018); XP055443764, Dec. 1, 2004, 11 pages.

*Primary Examiner* — Fekadeselassie Girma
(74) *Attorney, Agent, or Firm* — Michael A. Glenn; Perkins Coie LLP

(57) ABSTRACT

A system for monitoring liquid intake of a user includes a monitor configured to determine an amount of liquid removed from a container, an interface configured to receive a vital parameter of the user of the system from a vital parameter sensor, and a prompter configured to prompt the user to drink as a function of the amount of liquid removed and of the vital parameter.

31 Claims, 17 Drawing Sheets

(51) Int. Cl.
*A47G 19/00* (2006.01)
*A47G 23/00* (2006.01)
*A61B 5/021* (2006.01)

(56) References Cited

U.S. PATENT DOCUMENTS

| | | | | |
|---|---|---|---|---|
| D856,083 S | * | 8/2019 | Lawson-Shanks | D7/507 |
| 2011/0033830 A1 | * | 2/2011 | Cherian | G09B 5/02 |
| | | | | 434/236 |
| 2012/0094261 A1 | * | 4/2012 | Hayn | A47G 23/16 |
| | | | | 434/247 |
| 2012/0216605 A1 | * | 8/2012 | Silveri | G01N 27/08 |
| | | | | 73/61.41 |
| 2014/0046596 A1 | * | 2/2014 | Chang | G16H 40/63 |
| | | | | 702/3 |
| 2014/0303790 A1 | * | 10/2014 | Huang | G06Q 50/22 |
| | | | | 700/281 |
| 2015/0259114 A1 | * | 9/2015 | Tussy | B65D 81/365 |
| | | | | 206/457 |
| 2015/0359364 A1 | * | 12/2015 | Sweeney | G01F 13/006 |
| | | | | 206/459.1 |
| 2016/0009537 A1 | * | 1/2016 | Orita | B67D 1/0004 |
| | | | | 222/144.5 |
| 2016/0143583 A1 | * | 5/2016 | Jeukendrup | G01F 1/10 |
| | | | | 600/301 |
| 2017/0022040 A1 | * | 1/2017 | Koretz | B67D 1/04 |
| 2017/0156540 A1 | * | 6/2017 | Wheatley | A47J 31/521 |
| 2017/0225821 A1 | * | 8/2017 | Hynes | B65D 1/0261 |
| 2017/0334704 A1 | * | 11/2017 | Koretz | B67D 1/0888 |
| 2018/0072553 A1 | * | 3/2018 | Lyons | B67D 1/0079 |
| 2018/0177325 A1 | * | 6/2018 | Lyons | A47J 31/002 |

\* cited by examiner

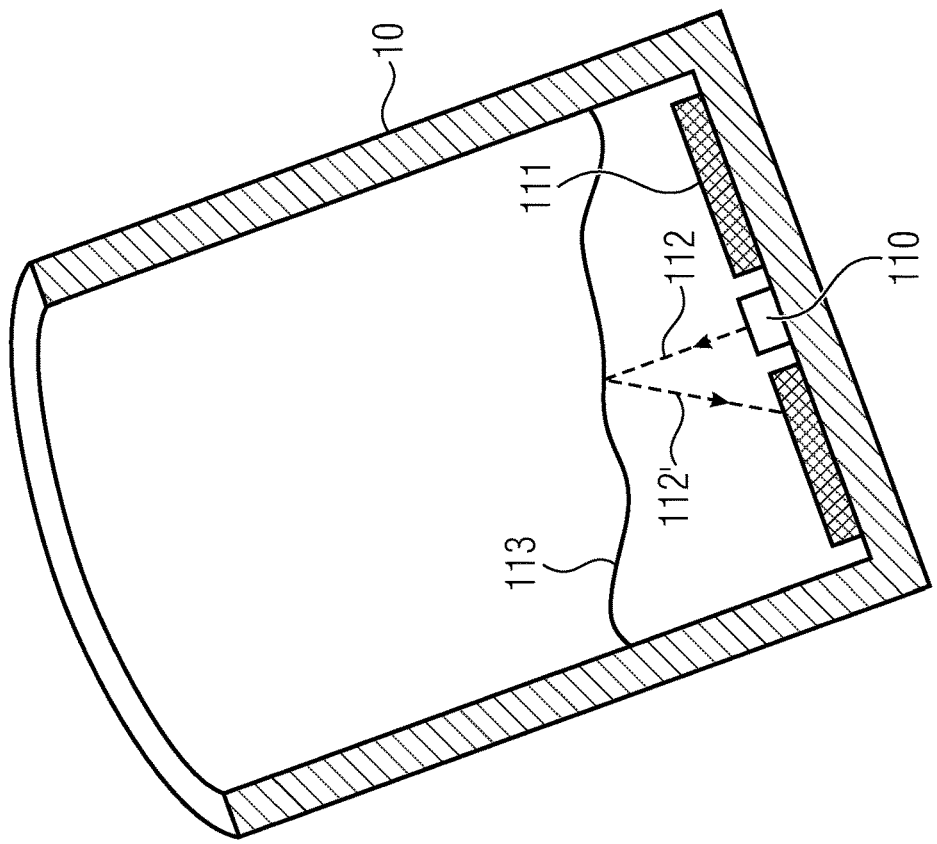
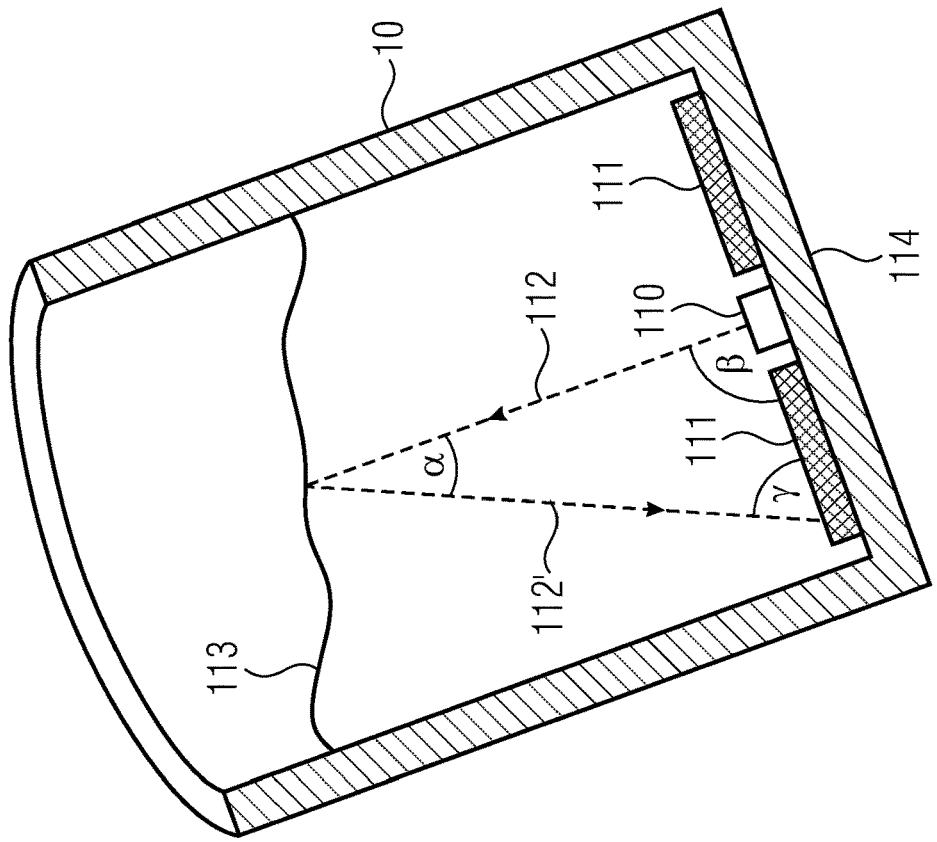
Fig. 14A
Fig. 14B

SYSTEM FOR MONITORING THE LIQUID INTAKE OF A USER AND METHOD OF OPERATING THE SYSTEM

CROSS-REFERENCES TO RELATED APPLICATIONS

This application is a continuation of copending International Application No. PCT/EP2017/070794, filed Aug. 16, 2017, which claims priority from German Application No. DE 102016215615.2, filed Aug. 19, 2016, which are each incorporated herein in its entirety by this reference thereto.

The present invention relates to a system of monitoring liquid intake of a user as well as to a method of operating same. Embodiments show a socket which is connected to a container and performs said monitoring. Further embodiments show technical means for coupling to a receptacle, or as a receptacle, for recording, evaluating, analyzing and storing the amount of liquid that has been drunk, or the supply of liquid. The technical means may be equipped with an alert and reminder function.

BACKGROUND OF THE INVENTION

Previous systems for monitoring liquid intake have enabled liquid intake to be generally determined, or determined on average, exclusively on the basis of an amount of liquid supplied to or removed from the container. To this end, the container may be placed upon a coaster, e.g., within which the evaluation is performed. However, in this manner it is not possible to determine liquid intake in a manner that is specific to an individual. Also, the system is highly prone to errors since the glass is placed next to the coaster inadvertently or due to forgetfulness, for example, e.g., with elderly people, and therefore, accurate filling-level information of the glass cannot be consistently determined.

SUMMARY

According to an embodiment, a system for monitoring liquid intake of a user may have: a container, a vital parameter sensor, a monitoring means configured to determine an amount of liquid removed from the container; an interface configured to receive, from the vital parameter sensor, a vital parameter of the user of the system; and a prompting means configured to prompt the user to drink as a function of the amount of liquid removed and of the vital parameter, wherein the monitoring means, the interface and the prompting means are arranged within a socket configured to receive the container, wherein the container is formed of a transparent material, wherein the prompting means is configured to couple light into the container for prompting purposes, and wherein the container includes scattering centers configured to scatter the light coupled in, and wherein the container includes a projection formed in the container bottom, and wherein the prompting means is configured to couple the light into the container at the projection.

According to another embodiment, a system for monitoring liquid intake of a user may have: a container exhibiting a projection or a curvature on a bearing surface, said projection or curvature being formed as a part of the container bottom, so that stability of the container is reduced when the container is placed down onto the bearing surface; a socket configured to receive the container so that the container can be placed down in a stable manner in connection with the socket; a monitoring means configured to determine an amount of liquid removed from the container; and a prompting means configured to prompt the user to drink as a function of the amount of liquid removed, wherein the monitoring means and the prompting means are arranged within the socket.

According to another embodiment, a system for monitoring liquid intake of a user may have: a container for receiving liquid; a level meter for measuring the filling level of the liquid contained within the container, wherein the level meter is an optical level meter including at least one emitter for emitting electromagnetic radiation and at least one receiver for receiving the emitted electromagnetic radiation; a monitoring means configured to determine an amount of liquid removed from the container; and a prompting means configured to prompt the user to drink as a function of the amount of liquid removed, wherein the emitter is arranged at the container such that the emitted electromagnetic radiation impinges upon the liquid surface, adjoining the surroundings, of the liquid contained within the container, wherein the receiver is arranged at the container such that a portion, reflected at the liquid surface, of the electromagnetic radiation emitted by the emitter is receivable by the receiver; and wherein at least one of the emitter and the receiver is arranged at a container bottom of the container.

According to another embodiment, a method of operating a system for monitoring liquid intake of a user may have the steps of: determining an amount of liquid removed from a container by means of a monitoring means, said container being formed of a transparent material; receiving a vital parameter of a user of the system from a vital parameter sensor by means of an interface; prompting the user to drink, as a function of the amount of liquid removed and of the vital parameter, by means of a prompting means, and coupling light into the container for prompting purposes, the container including a projection formed in the container bottom, wherein the light is coupled into the container at the projection, and the container including scattering centers configured to scatter the light coupled in.

According to another embodiment, a method of operating a system for monitoring liquid intake of a user may have the steps of: connecting a container having a projection or a curvature on a bearing surface, said projection or curvature being formed as a part of the container bottom, so that stability of the container is reduced when the container is placed down onto the bearing surface, to a socket configured to receive the container, so that the container can be placed down in a stable manner in connection with the socket; determining an amount of liquid removed from the container by means of a monitoring means; and prompting the user, as a function of the amount of liquid removed, by means of a prompting means, wherein the monitoring means and the prompting means are arranged within the socket.

According to another embodiment, a non-transitory digital storage medium may have a computer program stored thereon to perform the inventive methods, when said computer program is run by a computer.

Embodiments of a first aspect show a system of monitoring liquid intake of a user which comprises monitoring means, an interface and prompting means. The monitoring means may determine an amount of liquid removed from a container. The interface is configured to receive a vital parameter of a user of the system from a vital parameter sensor. In addition, the prompting means may prompt the user to drink as a function of the amount of liquid removed or of the vital parameter or, alternatively, of a plurality of vital parameters.

The present invention is based on the idea of determining a personalized, or individual, optimum amount of liquid for a user while taking into account (continuous) measurement of vital parameters of the user. In addition, the system is capable of adaptively adjusting to the person's current circumstances of life. For example, it may be ascertained, e.g., via the pulse frequency or the sweat that has been secreted whether a person is doing sports and/or is sweating a lot and therefore has increased liquid requirement, or whether the person is sleeping, for example, and thus is having a smaller requirement of liquid. This is possible by recording the calculation of the amount of liquid taken in while taking into account vital parameters that have been provided so as to calculate the amount of liquid to be taken in on the basis of a determined liquid requirement and of the actual amount of liquid taken in. If the amount of liquid that has been determined as having to be taken in exceeds a limiting value, or threshold value, the user will be prompted to drink.

Embodiments show that the monitoring means, the interface and the prompting means are arranged within a socket configured to receive the container. Thus, the socket may take over calculation of whether or not the threshold value for signaling that liquid is to be taken in by the user and/or for prompting the user to drink is reached, or may take over prompting the user per se.

Embodiments of a second aspect show a system of monitoring a user's liquid intake that comprises a container, a socket, monitoring means and prompting means. The container exhibits a projection or a curvature at a bearing surface, so that stability of the container is reduced when the container is placed down on the bearing surface. The socket is configured to receive the container, so that the container may be stably placed down in connection with the socket. The monitoring means determines the amount of liquid removed from the container, the prompting means being configured to prompt the user to drink as a function of the amount of liquid removed.

This is advantageous since inadvertent placing down or using the container without the socket, wherein at least a current amount of liquid contained within the container is sensed, may be avoided. Thus, it is ensured that the container is used exclusively in connection with the socket and that any gaps in monitoring the person's liquid intake are prevented, or do not arise. It the embodiments, the system in accordance with the second aspect advantageously comprises an interface which may receive a vital parameter of a user of the system at a vital parameter sensor, the prompting means further being configured to prompt the user to drink as a function of the amount of liquid removed and of the vital parameter. In accordance with an embodiment, the monitoring means and the prompting means may be configured within the socket. This advantageous since in this manner, in accordance with the first aspect, adaptive and personalized determination of the useful amount of liquid may be performed, and the amount of liquid that has already been taken in cannot be distorted by any error in operating or handling the systems since it is impossible or very difficult to place the cup down without the socket.

For example, an effective floor space of the container may be reduced by, e.g., more than 60%, more than 75% or more than 90% as compared to a maximum cross sectional area of an area of the container which may receive a liquid. Alternatively to the maximum surface area, it is also possible to use, as a comparative value, an average cross sectional area of the liquid reception area of the container, the reduction of the effective floor space being related to said comparative value.

The further embodiments represent advantageous implementations with regard to the two above-mentioned aspects. For example, embodiments show that the prompting means can prompt the container, the vital parameter sensor or a transceiver and/or a mobile device to prompt the user to drink by visual, auditive or tactile means. In terms of visual prompting, the container may be formed of a transparent material, for example, the evaluation means being configured to couple light into the container for the purpose of prompting (of the container). In addition, the container may comprise scatter centers configured to scatter the light coupled in and, thus, to reinforce visual prompting. In accordance with further embodiments, the container may also have a projection into which the evaluation unit couples the light into the container. This is advantageous since in this manner, coupling in of the light is performed perpendicularly to a viewing direction of the viewer looking into the container, or perpendicularly to a direction of opening of the container, and since the user is thus not disturbed, or dazzled, by the source of light coupling in. Since during drinking, the user's look is directed into the glass almost perpendicularly, arranging the LED in parallel with the direction of opening of the container may result in the user being dazzled. To avoid this, the LED may also be arranged horizontally or perpendicularly or diagonally, as was described above.

In accordance with further embodiments, the socket may comprise a fastening mechanism which firmly connects the container to the socket, e.g., mechanically or magnetically, in an operating state. This is advantageous since in this manner, misuse of the system is avoided which may occur, e.g., in that the user removes, and drinks, liquid from the container without said removal being detected by the monitoring means or the sensors. Then the container is not consistently connected to the evaluation means, which will thus impede or prevent continuous filling-level measurement of the container. In accordance with further embodiments, the socket may comprise a detection unit configured to identify the container in an operating state and to distinguish it from further containers, each of which has a specific filling quantity. The distinction made on the part of the monitoring means enables determining a container-specific removed amount of liquid and associating the container with the respective user. This is advantageous since in this manner the amount of liquid removed is not stored in a socket-specific manner but is stored in connection with (or within), e.g., a user profile, so that an identifying feature such as an electronic chip, for example, is identified by the socket, and so that in the event of an (inadvertent) exchange of the sockets of two or more containers, the correct amount of liquid drunk will be associated with the user belonging to the respective container rather than with the user who used the socket before.

In accordance with further embodiments, the system comprises an inclination sensor, or inclinometer, configured to sense an angle of inclination (tilt angle) of the container. This is advantageous, e.g., when the amount of liquid removed is determined on the basis of a weight of the liquid. By lifting and tilting the container (with or without the socket), the amount of liquid contained within the container cannot be accurately determined during this time period. Thus, said (time) period is excluded from monitoring of the filling quantity. A comparison between the quantity of liquid prior to lifting and/or tilting, and a comparison following placement may reconsolidate, or re-determine, the amount of liquid that was removed, or taken in, in the meantime. Detecting tilting of the container may also represent protection against erroneous measurements, e.g., when liquid is deliberately or inadvertently (e.g., when the container is knocked over) spilled or poured out. A combined chip for measuring inclination/acceleration may possibly support verification here.

This is advantageous since in this manner, measurement of the current intake of liquid is improved once again.

BRIEF DESCRIPTION OF THE DRAWINGS

Embodiments of the present invention will be detailed subsequently referring to the appended drawings, in which:

FIG. 14A shows a container comprising a level meter in accordance with an embodiment, FIG. 14B shows the container of FIG. 14A which has a lower filling level of the liquid contained within the container.

DETAILED DESCRIPTION OF THE INVENTION

Figure 1:
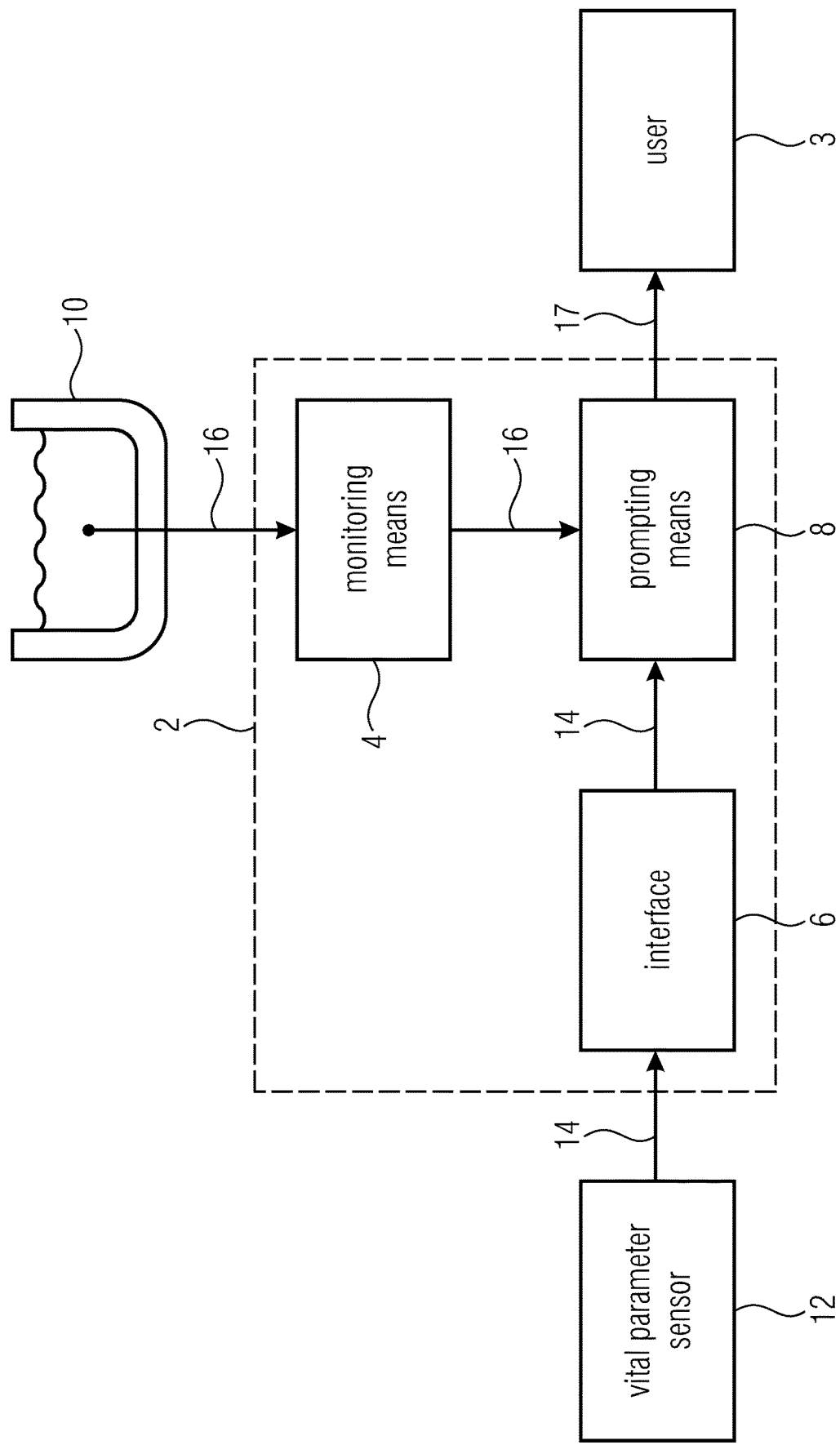
FIG. 1 shows a schematic representation of the system for monitoring intake of an amount of liquid in accordance with a first aspect.

In the following description of the figures, elements which are identical or have identical actions will be provided with identical reference numerals, so that their descriptions in the different embodiments are mutually exchangeable.

FIG. 1 shows a schematic representation of a system 2 for monitoring intake of liquid of a user 3. The system 2 comprises monitoring means 4, an interface 6 and prompting means 8.

The monitoring means 4 is configured to determine an amount of liquid removed 16 from a container 10. The interface 6, e.g., a wireless interface, is configured to receive a vital parameter 14 of the user 3 of the system 2 from a vital parameter sensor 12.

In addition, the prompting means 8 is configured to prompt the user 3 to drink as a function of the amount of liquid removed 16 and of the vital parameter 14.

The vital parameter sensor 12 is, e.g., a pulsometer, a blood pressure meter, a sweat detector, a pedometer, etc.

In addition, the container 10 may be placed down, in accordance with an advantageous embodiment, into a matching socket, which socket may comprise the monitoring means 4, the interface 6 and/or the prompting means 8.

The sweat, or perspiration, sensor measures, e.g., dehydration of the body so as to determine with a very high level of accuracy, on the basis of the amount of sweat emitted, and/or of an analysis (of the composition) of the sweat, the amount of liquid needed by the body. Implicitly, said information may also be calculated, for example, from the movement, or a movement profile, and from the calorie consumption derived therefrom.

Figure 2:
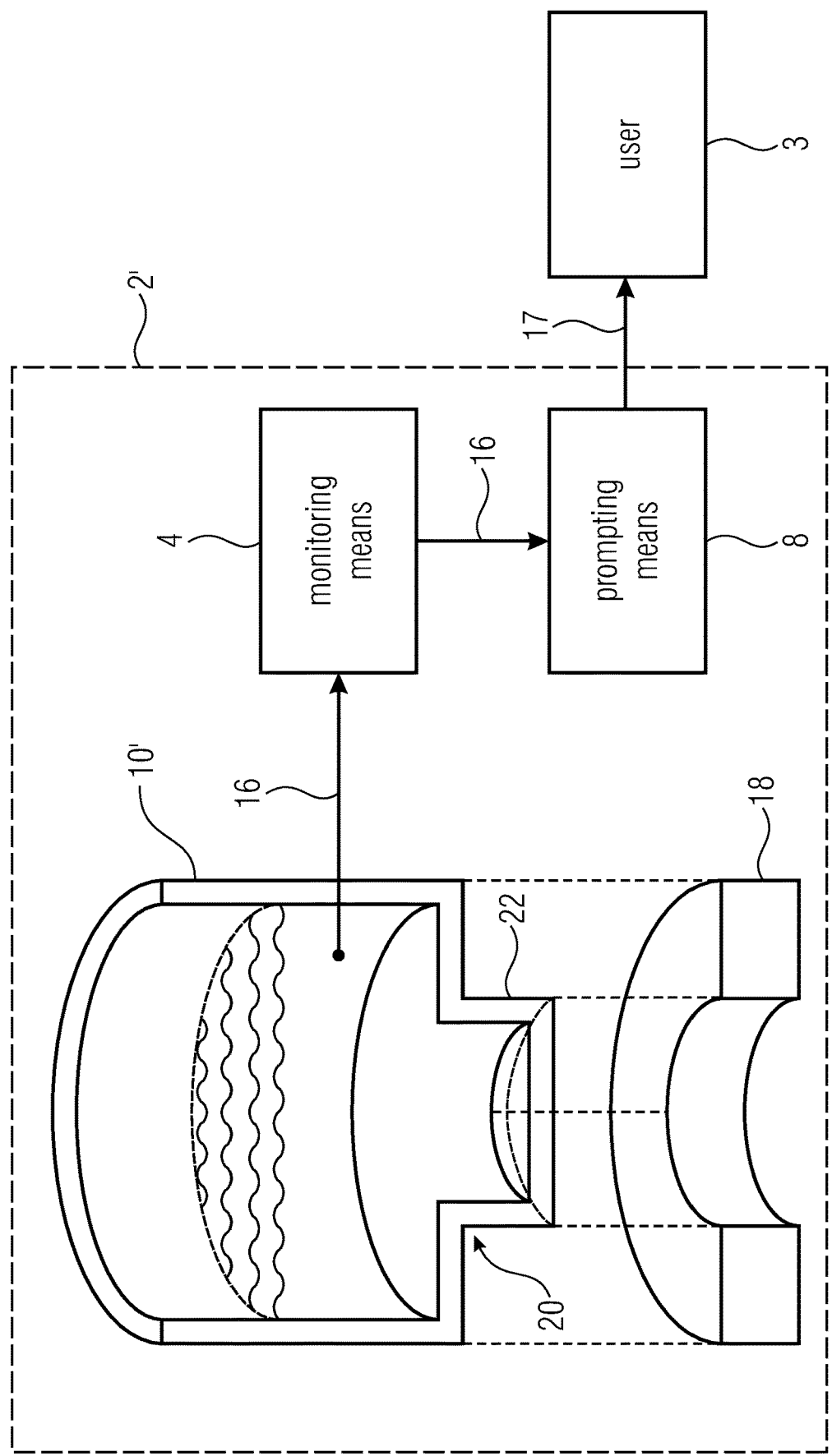
FIG. 2 shows a schematic representation of a system for monitoring a removed amount of liquid on the part of a user in accordance with a second aspect.

FIG. 2 shows a schematic representation of a system 2' for monitoring liquid intake of a user 3. The system 2' comprises a container 10', a socket 18 as well as the monitoring means 4 and the prompting means 8.

On a bearing surface 20, the container 10' comprises a projection 22 or a curvature 22, so that stability of the container 10' is reduced when the container 10' is placed down onto the bearing surface 20. In addition, the socket 18 is configured to receive the container 10', so that the container 10' may be placed down in a stable manner in connection with the socket 18.

The monitoring means 4 is configured to determine an amount of liquid removed from the container 10', and the prompting means 8 is further configured to prompt 17 the user 3 to drink as a function of the amount of liquid removed 16.

In accordance with embodiments, the system 2' may further comprise an interface configured to receive a vital parameter of user system from a vital parameter sensor 12, the prompting means 8 being configured to prompt the user to drink as a function of the amount of liquid removed and of the vital parameter.

In addition, the monitoring means 4 and the prompting means 8 may be implemented within the socket 18. Thus, in this embodiment, the features and, therefore, also the advantages of system 2 and of system 2' may be combined.

The following embodiments relate to both the system 2 in accordance with the first aspect of FIG. 1 and to the system 2' in accordance with the second aspect of FIG. 2. Moreover, the reference numerals for the system 2 and/or 2' and for the container 10 and/or 10' will be mutually exchangeable below unless explicitly stated otherwise.

Figure 3A:
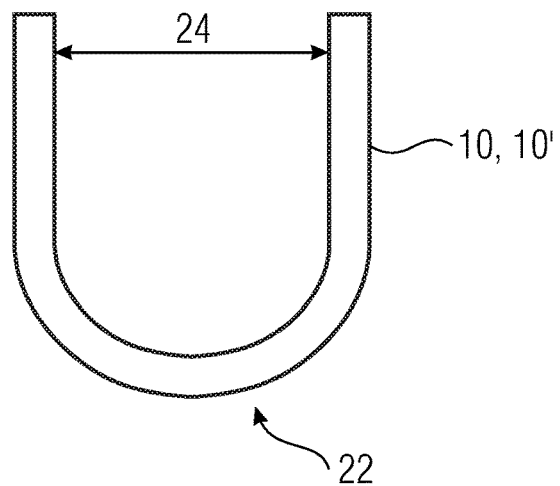
FIGS. 3A-3C show schematic representations of possible shapes of a container having reduced floor space.
Figure 3B:
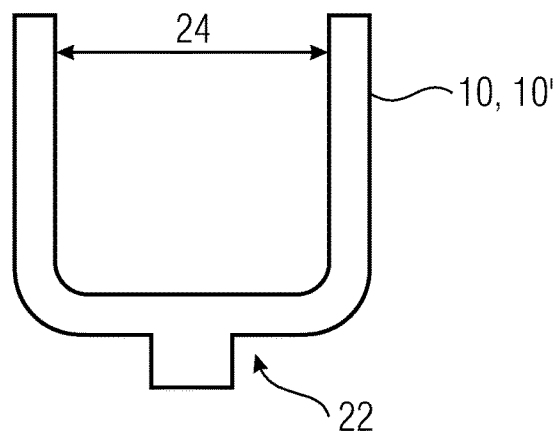
Figure 3C:
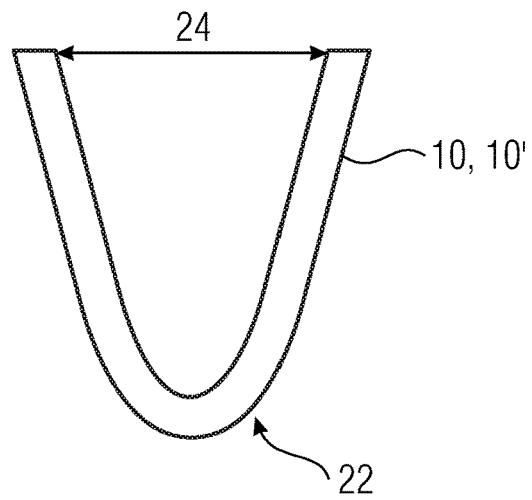

For example, FIGS. 3A-3C show different shapes of the container 10, 10' as may be used with the socket 18 of aspect 1 and with the socket 18 of aspect 2.

Specifically, the containers of FIGS. 3A to 3C comprise projections or curvatures 22 so as to reduce stability of the container 10, 10' when said container 10, 10' is placed down onto its placing surface. For example, FIGS. 3A and 3C depict a curvature 22 in the bearing surface of the container 10, 10', and FIG. 3B shows a projection 22 as the bearing surface of the container 10, 10'.

The effective resting surface and/or bearing surface, i.e. that part of the curvature 22 or of the projection 22 which touches the surface of the placing surface when the container 10, 10' is placed down onto a placing surface, is smaller than 60% and/or smaller than 75% or smaller than 90% than a cross-sectional area 24 of the container 10, 10'. The cross-sectional area 24 may be, e.g., the largest possible surface area that the surface of the liquid contained within the container 10, 10' may have, or may be an average surface area of the surface of the liquid contained within the container 10, 10'.

Figure 4:
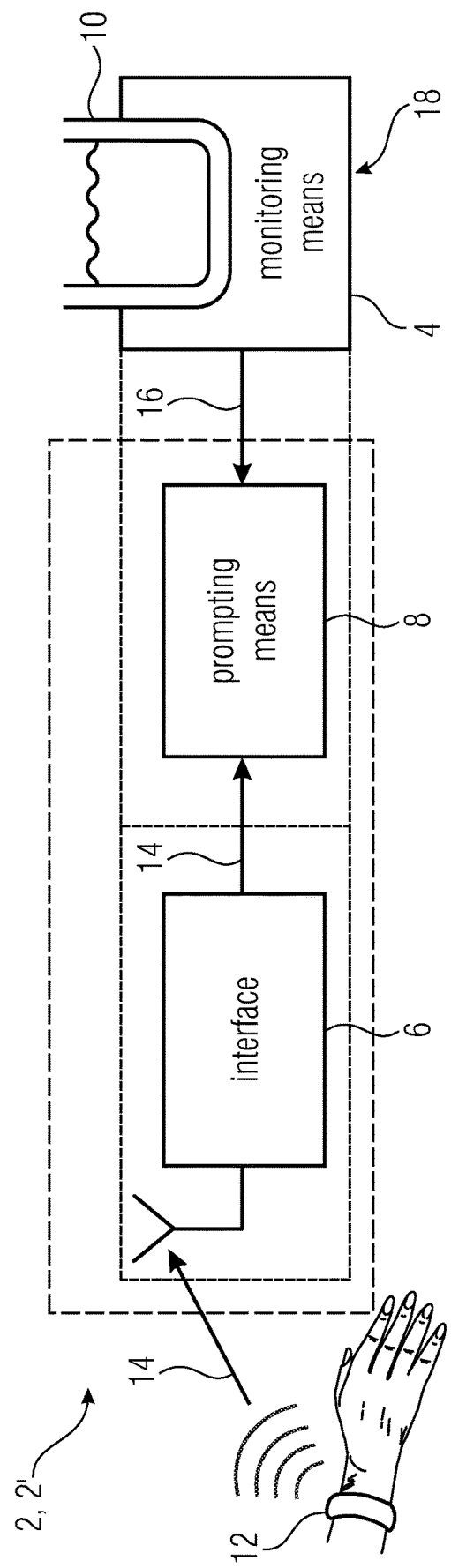
FIG. 4 shows a schematic representation of the system in accordance with an embodiment.

FIG. 4 shows the system 2, 2' in accordance with a further embodiment with the focus on the arrangement of the interface 6 and the prompting means 8. For example, the prompting means 8 may be arranged within the monitoring means 4. Additionally, the interface 6 may also be arranged within the monitoring means 4, whereby an advantageously wireless connection between the prompting means 8 and the interface 6 to the monitoring means 4 is eliminated, or avoided, and, therefore, potential interference with said connection is avoided. Moreover, installation of the system may be facilitated for an (inexperienced) user.

In accordance with further embodiments, however, the interface 6 and the prompting means 8 may also be arranged at a distance from the monitoring means 4 and the vital parameter sensor 12. For example, it is possible to form a relay station for a plurality of vital parameter sensors 12 and/or a plurality of monitoring means 4, said relay station performing the data exchange between the vital parameter sensor(s) 12 and the one or more monitoring means 4. For example, a user may also use several vital parameter sensors 12 so as to determine, when combining the vital parameters determined, improved prediction of the minimum, or optimum, amount of liquid to be taken in.

In addition, the user may also use several systems in parallel, which exchange, e.g., via the relay, the amounts of liquid removed which have been determined, or the user may transmit same to the relay or to a remote (central) server for evaluation. For example, evaluation of the vital parameters and/or of the filing level of the container 10, 10' may be effected in the remote device, it being possible for the data to be transmitted from the vital parameter sensor 12 and/or from the monitoring means 4 to the remote device in a wired or wireless manner.

Wireless connection may be performed, e.g., by means of WiFi, Bluetooth, NFC, or similar suitable data transmission methods. In other words, the computing power of the system for evaluating the relevant data may be (fully) located within the remote device.

In accordance with further embodiments, the prompting means 8 may be configured to prompt the user to drink, if need be, directly via the remote device. However, it is also possible to transmit the result of the evaluation, i.e., a signal that the user is to be prompted to drink, to the monitoring means 4 and/or to the container 10, 10' or to the vital parameter sensor 12. For example, the vital parameter sensor 12 may comprise a display, a vibrating alert and/or an LED or a different illuminant so as to directly prompt the user to drink in immediate proximity.

Moreover, it is also possible for the container 10, 10' to take over the task of prompting. This will be explained in more detail below with reference to FIG. 8, for example.

Figure 5:
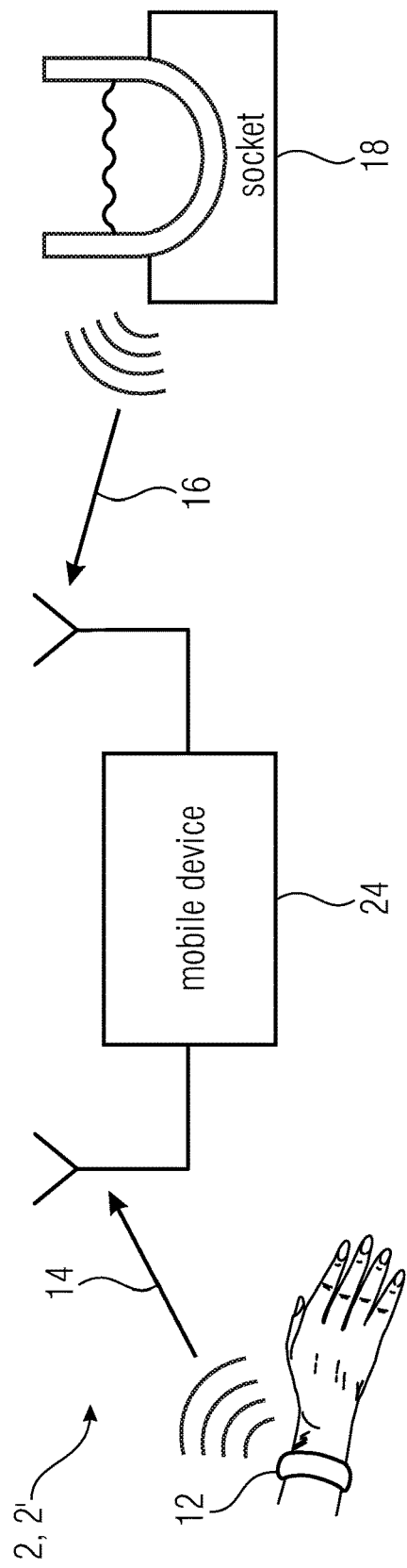
FIG. 5 shows a schematic representation of the system comprising a mobile device.

FIG. 5 shows the system 2, 2' in accordance with a further embodiment. Here, a mobile device 24, e.g., a transceiver or a mobile phone, is arranged in the transmission link between the vital parameter sensor 12 and the container 10, 10'. Here, the mobile device 24 may act as a relay, for example, and may receive the vital parameter 14 and/or the amount of liquid removed 16, and may optionally evaluate same.

Evaluation may also be performed centrally on a remote server. For example, a mobile app (mobile application), or a program performed on a mobile phone 24, may receive and log the received vital parameters 14 as well as the amount of liquid removed 16, e.g., at regular time intervals or upon a change in the amount of liquid.

In addition or as an alternative, the data to be logged may be transmitted to a centrally arranged server. On the basis of the vital parameters 14 received and of the amounts of liquid removed 16, the invitation and/or prompting of the user to drink may be effected at the mobile device 24, at the vital parameter sensor 12, at the container 10, 10' and/or at the socket 18 within which the container 10, 10' is arranged.

What applies alternatively or additionally to all embodiments of the present disclosure is that the container 10, 10' and/or the socket 18 may each be configured to directly communicate to a reception and evaluation unit such as a central cloud server, for example. In other words, with such an embodiment, transmission, or relay, of data by means of the mobile device 24 which was mentioned at the outset and acts as a relay might be dispensed with.

For example, such containers 10, 10' and/or sockets 18 may each comprise an integrated control unit (e.g., CPU, ASIC, etc.) which is capable of connecting directly to a central cloud server, e.g., by means of a GSM module or a freely available network such as LORA.

A control unit integrated within the container 10, 10' and/or the socket 18 may be capable of being programmed directly, for example. Alternatively or additionally, the control unit might be configured to sense user data such as age, size, sex, etc., and to optionally perform independent calculations based thereon. Alternatively or additionally, the control unit may be configured to transmit usage data to the server and to optionally acquire and install firmware updates.

Thus, the container 10, 10' and/or the socket 18 would be "IoT"-capable (IoT=Internet of Things), possibly also without there being an additional relay such as the above-mentioned mobile device 24, for example.

Irrespectively of whether the container 10, 10' and/or the socket 18 communicates directly or indirectly, by means of a relay, with a reception and evaluation unit, it may be advantageous, for evaluating and/or for determining whether the user is to be prompted to drink, to draw upon the history of the data recorded, so that a recommendation, e.g., for the time that has elapsed since the user woke up, is output. Waking up may be determined, for example, also by the vital parameter sensor 12 and/or by means of the recorded vital parameters 14.

In other words, the prompting means 8 may be configured to prompt the container 10, 10', the vital parameter sensor 12 or the mobile device 24 to prompt the user to drink, in a visual/optical, auditive/acoustic, or tactile/haptic manner. To this end, the prompting means 8 may be arranged within the mobile device 24, for example.

In accordance with further embodiments, the system may be implemented into an existing health app which has optionally already been configured to obtain data from a vital parameter sensor 12. Thus, a supplementation of the app by a method is possible which performs evaluation of the already existing vital parameters 14 on the basis of the amounts of liquid removed 16 which have been received, and which derives therefrom a recommendation for taking in the liquid. Thus, it is with a small amount of expenditure that an existing system may be supplemented by the ability to output individual drinking recommendation for the user.

The user may also enter, or sense, personal data such as the age, sex, size, weight, sporting activities, etc., in the mobile app. Said parameters may be taken into account in calculating the recommended, or proposed, amount of liquid to be drunk. Additionally or alternatively, geo data and/or the external temperature may be taken into account in the calculation.

In accordance with embodiments, the mobile app or also a web interface and/or an internet application may obtain, by means of said personal data, a personalized proposal for liquid intake. For example, individuals of different age groups have different physical requirements in terms of the intake of food and liquid.

By sensing the contents of the container (by scanning the GTIN or by means of a quick scan) and by determining, e.g., minerals, nutrients, etc., the user may be provided with advice, which corresponds to his/her personal parameters, in terms of his/her drinking behavior (for example, liquids with a low calcium content are disadvantageous for elderly people, etc.). This might be effected, e.g., via a corresponding display in the application of the smartphone or within the framework of the web application.

In accordance with further embodiments, the user has the possibility at any time, via the mobile application, to have the "actual data" and the historic data (e.g., 90 days) displayed to him/her. However, the application may also directly transmit each set of data to a central database. Said database enables the user to have the data displayed to him/her in a web application over an extended time period (e.g., 360 days).

Against said background, the data in question here are personalized data that are stored such that they are protected (data protection) accordingly. All data may be transferred into a further database in a de-personalized manner, i.e., without containing any personal information, so as to be able to derive empirical statements about the overall user behavior of all persons using the system.

Upon request, the user may have an extract therefrom shown to him/her in which he/she may compare himself/herself with persons of the same sex, the same age group, etc. This "gaming effect", i.e. the comparison with other users, results in the advantage that the user enters into competition, as it were, with persons of his/her reference group and thus drinks more "voluntarily".

All the aspects described which might be performed by means of a mobile app might be performable, alternatively or additionally, with the previously mentioned control unit integrated into the container 10, 10' and/or the socket 18, which also may be a combined control and communication unit.

FIGS. 6a-6e show schematic cross-sectional views of the container 10, 10' in connection with the socket 18. In FIGS. 6a to 6e, various embodiments of the socket 18 are also shown.

For example, embodiments will be shown below wherein the monitoring means 4 and/or the socket 18 comprise(s) a sensor 32 configured to determine a current filling level of the container 10, 10'.

For example by means of a time sequence of current filling levels determined of the container 10, 10', the monitoring means 4 may determine the amount of liquid removed from the container 10, 10'. With regard to FIGS. 6a-e, it is explained that the monitoring means 4 is configured, in embodiments, to determine the amount of liquid removed from the container 10, 10' (in particular) by means of capacitive measurement, by means of optical measurement, by means of ultrasound, by means of radar, by means of a change in the weight, by means of a run-time measurement, and/or by means of conductivity measurement, thus, the above-mentioned sensor 32 may be a sensor which performs the measurement in accordance with the method mentioned.

Figure 6A:
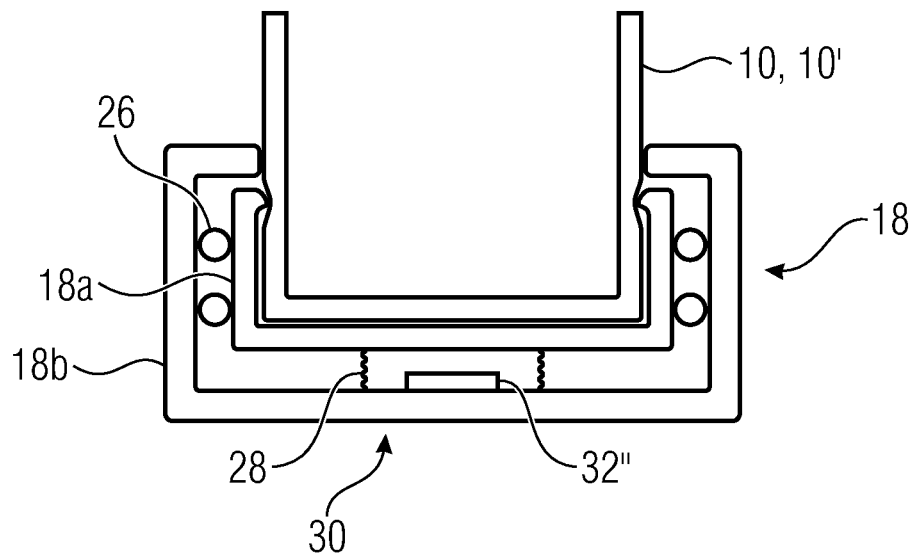
FIGS. 6A-6E show schematic representations of various sensor arrangements for determining the amount of liquid contained within the container.

FIG. 6a shows the socket 18 comprising a receiving element 18a for the container 10, 10' as well as a frame element 18b forming an outer limitation of the socket 18.

The receiving element 18a may be movably arranged within the frame element 18b, e.g. via ball bearings 26. In addition, spring elements 28 may be arranged between the receiving element 18a and the frame element 18b, said spring elements 28 which retain the container 10, 10' in a first position in a non-filled, or empty, state, and which yield in a filled state so as to retain the container 10, 10' in a second position. In the second position, the container 10, 10' is consequently arranged closer to a floor space 30 of the socket 18 than it is in the first state.

Measurement of the filling level of a liquid contained within the container 10, 10', which allows conclusions to be drawn as to the amount of liquid removed, may be effected, e.g., via the weight force of the container 10, 10', e.g. by means of one or a plurality of strain gauges mounted on the spring element 28, or may be capacitively effected via the change in the distance between the receiving element 18a and the frame element 18b. For capacitive measurement, an electrode 32" may be arranged between the receiving element 18a and the frame element 18b, said electrode 32" determining the distance between the receiving element 18a and the frame element 18b.

In accordance with an embodiment, a piezo element, or a piezo sensor, may also be arranged, in addition or as an alternative to the spring element 28, between the receiving element 18a and the frame element 18b, said piezo element or piezo sensor being able to determine a weight force of the container 10, 10' on the basis of its deformation.

Figure 6B:
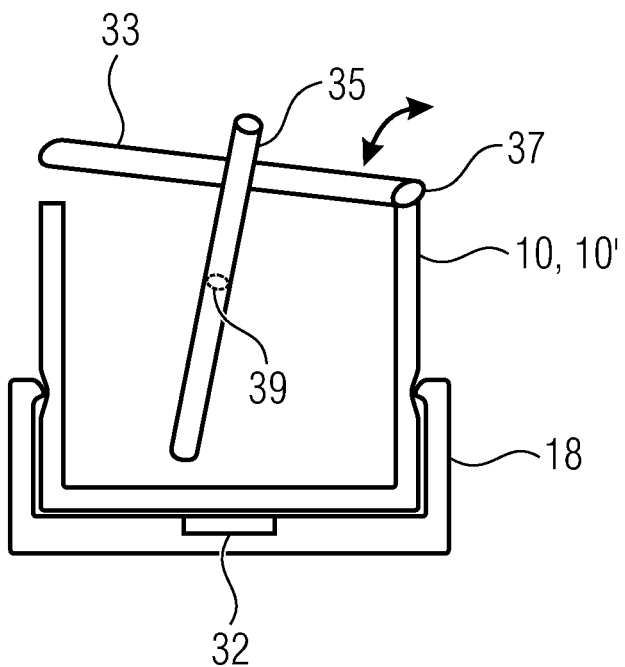

FIG. 6b shows the socket 18 comprising the sensor 32 configured to determine the filling level within the container 10, 10' from the floor, or from a bearing surface, of socket 18. For example, the filling level may be measured, e.g., by means of a reflection at the boundary layer between (a surface of) the liquid contained within the container and the surrounding medium, typically air, by using electromagnetic waves or radiation, i.e., e.g., by using ultrasound, optical radiation and/or light, or radar.

For example, run-time measurement between the emitted electromagnetic radiation and the received, reflected electromagnetic radiation may allow a conclusion to be drawn as to the filling level of the container 10, 10'.

A measurement method starting from one side of the container 10, 10', i.e. from the bottom, for example, may be advantageous, in particular, in a humid environment that is present here since thus, the entire electronics of the system may be advantageously be implemented within a circuit board inside the socket 18. In this manner, error-prone connections and/or contacts between different circuit boards or partial systems arranged at a distance from one other are avoided, in particular in humid environments. A single fixedly soldered circuit board without external wires here offers advantages with regard to a low level of fault liability.

In addition, the container 10, 10' may also comprise a lid 33 within which, in accordance with embodiments, also the sensor 32 and/or part of the sensor 32 may be arranged.

Thus, it is possible, for example, to detect an electromagnetic wave, e.g. a light beam that undergoes refraction from the transition of the liquid into the container 10, 10' into the surrounding air, and to determine the filling level of the liquid contained within the container 10, 10' by means of the deflection and, optionally, of the angle of incidence.

In accordance with a further embodiment, a (capacitive) proximity sensor 32 may be arranged inside the lid 33 which may determine a distance of the sensor 32 from the surface of the liquid contained within the container 10, 10' and thus may determine the filling level.

A sensor 32 inside the lid 33 may advantageously be combined with a further sensor 32 which indicates the closure of the lid 33 so that said measurement is performed and/or evaluated when the lid 33 is closed.

The lid 33 may have the shape of a drinking aid, for example, so that the container 10, 10' may form a feeding cup when combined with the lid 33.

In accordance with embodiments, the lid 33 for the container 10, 10', i.e., e.g., a glass or a carafe or a bottle, may clean any liquids contained therein, such as tap water, for example. To this end, the lid 33 may comprise a UV lamp which emits UV radiation so to free the liquid from any germs contained therein.

For supplying the lid 33 and/or the UV lamp with energy, a momentum generator or a photovoltaic cell may be arranged, in a manner similar to that of the socket 18, inside and/or on the lid 33, so that self-sufficient power supply of the lid 33 is possible.

Alternatively or additionally, the lid 33 may also be electrically connected to the socket 18 and/or to the monitoring means 4 or the prompting means 8. An electrical connection via an electric lead may be implemented, with a fold-open lid 33 which is connected to the container 10, 10' via a hinge 37 but is not separated therefrom by default, within or via the hinge 37 or in immediate proximity of the hinge 37.

In addition, the lid 33 may comprise a controller (or intelligence) which drives the UV lamp so as to prevent permanent UV light irradiation. For example, the controller may cyclically switch the UV lamp on and off, may switch the UV lamp off when the lid 33 is opened, or switched it on, as will be described below in detail, on the basis of a food and/or liquid analysis wherein a current germ load has been determined which exceeds a (default) limiting value.

In accordance with further embodiments, the prompting means 8 may also be implemented inside the lid 33, in addition or alternatively.

In addition to or instead of the container 10, 10'—here, a drinking bottle, in particular—the lid 33 may also signal the drinking recommendation by means of light, for example. Here, the lid 33 may be connected to the associated socket 18 accordingly via a wireless data link.

In addition, the lid 33 may comprise a passage for, e.g., a straw or any other drinking aid 35, wherein the amount of liquid drunk may be measured and/or verified via the amount of liquid flowing through. The drinking aid 35 may provide the determined amount of liquid flowing through to the monitoring means 4 for evaluation in a wireless manner or by means of a contact with the lid 33. It is via the same connection that power supply can also be established. The amount of liquid flowing through may be determined via a charge flow sensor 39 arranged inside the drinking aid. A lid 33 with and without drinking device 35 may also be used for a drinking glass, which glass here may also be employed, e.g., for "to go" beverages.

In other words, the system may comprise a drinking aid 35 configured to determine an amount of liquid flowing through which has been removed from the container 10, 10' by means of the drinking aid 35, and to provide to the monitoring means 4 the amount of liquid removed from the container 10, 10' by means of the drinking aid 35.

The monitoring means 4 may compare the amount of liquid removed from the container 10, 10' by means of the drinking aid 35 with the amount of liquid removed, which has been determined by means of one of the further methods described, of the container 10, 10' so as to determine an optimized amount of liquid removed. For example, minor inaccuracies in determining the amount of liquid removed may be minimized by means of averaging, for example, and in the event of a deviation larger than a typical tolerance of the measurement methods, a different type of removal of liquid, e.g. by means of pouring out the contents of the container 10, 10', may be ascertained.

Additionally or alternatively, the amount of liquid removed from the container 10, 10' by means of the drinking aid 35 may also be used as a reference, i.e. as the single amount of liquid removed for evaluation within the monitoring means 4. For example in combination with a fixedly attached lid 33 which is not provided for being taken off during drinking, the amount of liquid removed from the container 10, 10' by means of the drinking aid 35 may correspond with the highest level of accuracy to that amount of liquid that has been taken in by the user.

Figure 6C:
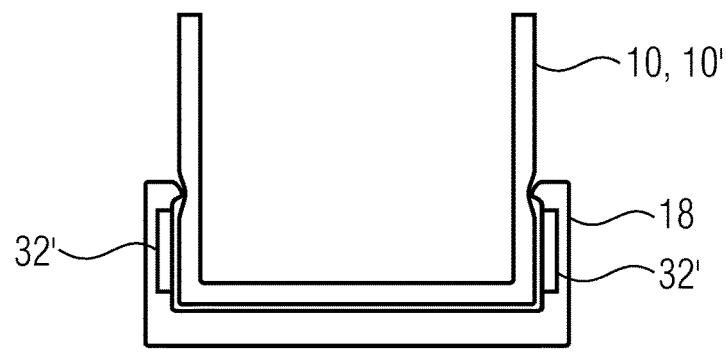

FIG. 6c shows the socket 18 with sensors 32', which in the embodiment shown are placed on the side walls of the container 10, 10' and/or of the socket 18.

Advantageously, the sensors 32' here are arranged entirely across a complete height of the container 10, 10' so that emitted electromagnetic radiation and/or signals of a sensor element 32' may be received at the oppositely located sensor element 32'.

If the surface and/or the boundary layer between the liquid and the surrounding air is located within the detector surface area, the current filling level of the liquid contained within the container 10, 10' may be determined via the run-time differences of the emitted signals through the air and within the liquid.

Figure 6D:
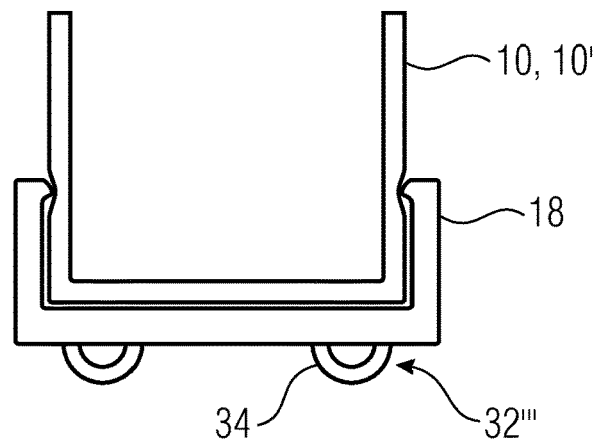

FIG. 6d shows the socket 18 with bearing elements 34, e.g. feet or knobs which may be arranged below the bearing surface of the socket 18.

Similarly to what was already shown in FIG. 6a, it is within the bearing elements 34 that measurement of the contents of the container 10, 10' may be effected via a change in weight of the container 10, 10', which is measured by means of the sensor 32''' arranged within one or more bearing elements 34.

The sensor 32''' is a strain gauge, a piezo element, or a capacitive sensor, for example. This is advantageous since the bearing elements 34 may be connected to the socket 18 e.g. via a detachable connection such as a screwed or plug-type connection, for example, which is why the weight sensor 32''' may be replaced at low cost in case of a defect.

Figure 6E:
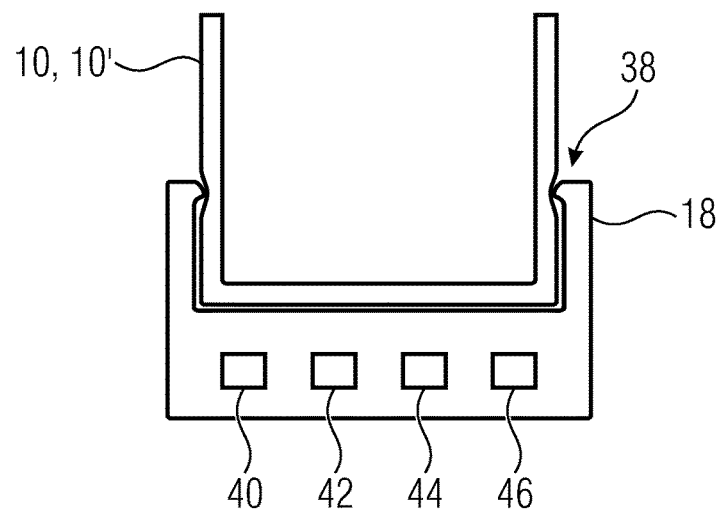

FIG. 6e shows the socket 18 with the container 10, 10' in accordance with a further embodiment; the elements and/or features described below may be arranged within the socket 18 individually or in any combination.

For example, FIG. 6e shows a fastening mechanism 38 configured to fixedly connect the container 10, 10' to the socket 18 mechanically or magnetically in an operating state.

Moreover, the container 10, 10' may be firmly, but not inseparably, connected to the socket 18 also via other (physical) forces. For example, it is advantageous for the connection to be firm enough so that lifting or a movement of the container 10, 10' will result, to the same degree, in lifting and/or a movement of the socket 18. Nevertheless it should be possible to separate the container 10, 10' and the socket 18 from each another, e.g. for cleaning or storing purposes. Therefore, the connection may also be performed by means of screwing, clamping or press fitting.

In addition, the socket 18 may comprise a detection unit 40 configured to identify the container 10, 10' in an operating state and to distinguish it from further containers 10, 10' each having a specific filling quantity.

The distinction made by the detection unit 40 enables the monitoring means 4 to determine a container-specific amount of liquid that was removed, and/or drunk, and to associate the container 10, 10' with the user related to it. This is advantageous since therefore, the sockets 18 are universally applicable for each container 10, 10' and, therefore, deliberate or inadvertent exchange of used containers 10, 10' and associated sockets 18 will nevertheless yield the same results for the user of the container 10, 10'.

To be recognized, the container 10, 10' may comprise, e.g., a specific code, e.g. in the form of an RFID tag or a QR code so as to enable the detection unit 40 to determine the current container 10, 10'.

In addition, it will then be advantageous to also determine associated vital parameters in a user-specific manner, so that it is also possible to determine, as a function of the vital parameters, whether or not the user is to take in liquid.

In embodiments, the socket 18 may additionally sense and set a temperature of the liquid contained within the container 10, 10'. To this end, the socket 18 may comprise a thermostat 42 configured to determine a temperature of the liquid and to warm up or cool down the temperature of the liquid to the value set in case there is a deviation from a reference value which has been set, e.g., by the user.

Warming and cooling and/or measurement may also be performed while setting a hysteresis. Thus, the socket 18 may provide for cool beverages in summer and for a pleasant temperature of a warm tea or other hot beverage in winter, for example.

In accordance with further embodiments, the system may comprise, e.g. within the socket 18, an energy supply unit 44 configured to supply the system 2, 2' with energy in a self-sufficient manner by means of solar technology, by means of energy harvesting, by means of a generator and/or of a momentum generator.

In other words, the system and/or the socket 18 may be operated in a manner in which it is free from a current source, or may be operated at least with reduced current consumption when the above-mentioned means for energy production are employed. In order to ensure continuous energy supply and to compensate for peaks and dips in energy supply, the energy supply unit may further comprise an accumulator, a capacitor or a further energy store which stores, or buffers, the energy.

For example for relatively small or low-cost systems, it is also possible, however, to provide external current supply permanently or for charging the energy storage, e.g. by means of a USB terminal or induction (e.g. via near-field communication (NFC)). However, with a view to ecological aspects, a self-sufficient or at least partly self-sufficient system is advantageous.

The battery and/or the accumulator may also be charged by means of RFID (radiofrequency identification), NFC (near-field communication), or USB (universal serial bus). Said energy supply may also be used for cooling or warming the beverage, e.g. by means of a Peltier element. Due to the potentially high energy consumption of the heating and/or cooling element, e.g. when large differences in temperature are to be overcome, separate current supply may also be provided for this purpose.

Further embodiments show the system for application in the catering trade.

Once the filling level of the glass 10, 10' falls below a predefined threshold value, the waitron and/or the landlord may be informed of this fact. Said recognition that the filling level of the glass 10, 10' has fallen below the predefined threshold value may be effected by means of the monitoring means 4. Signaling by means of the prompting means 8 may then be effected in a decentralized manner, e.g. at a central switch board, such as a service terminal for the waitrons, by corresponding notification on the part of the glass 10, 10' and/or the socket 18.

In other words, the prompting means 8 here may be arranged within the service terminal and may output a notification on the service terminal on the basis of the result of the monitoring means 4. Here, the waitron or the person handing out beverages may define and/or clearly associate the glass (container) 10, 10' and/or the socket 18 with a table number and a contents of the glass, for example. The seating area indoors and outdoors should be equipped with corresponding receivers which transmit corresponding notifications to the landlord, the persons handing out beverages, the waitrons, or a central terminal.

In addition or alternatively, the waitron may be equipped, in accordance with an embodiment, with a bracelet via which he/she is informed, e.g. by means of a vibration alert, that he/she is in the vicinity of an empty or almost empty glass 10, 10'. Here, the prompting means 8 may be arranged inside the bracelet. The waiter's bracelet here may scan, e.g., a predefined radius of, e.g. five meters and/or receive signals of the container/socket within said radius and may trigger corresponding signaling at the bracelet upon receipt of a signal of the monitoring means.

Both above-mentioned embodiments have an advantage for the guest in that he/she will not die of thirst and/or will be inclined to stay longer at the restaurant because of the good service, for the landlord in that possibly more beverages are sold or further products such as deserts etc. are bought, and for the waitron who benefits from increased earnings by being given a share of the turnover or by receiving more tip, and who will be able to react faster to the guests' wishes.

The glasses 10, 10' may be equipped with an RFID chip or an NFC chip for both methods, which chips may be mounted either inside or outside the glass 10, 10'. Thus, the monitoring means 4 may communicate with the prompting means 8, i.e. transmit a signal that the liquid level within the glass 10, 10' has fallen below the default threshold value.

Said chip may be the same RFID or NFC chip that is also used for charging the energy store within the socket 18 and/or the container 10, 10', as was described above.

In accordance with further embodiments, the socket 18 may comprise an inclination sensor 46 configured to sense an angle of inclination of the sensor 10, 10'. It is possible to verify, by means of the inclination sensor 46, whether or not somebody is currently drinking from the container 10, 10'. In those moments when somebody is drinking from the containers 10, 10', reliable measurement of the filling level of the container 10, 10' may be interfered with, which should be taken into account in the measurement.

In addition, minor deviations in the current filling quantity may be averaged, or compensated for, by comparing the filling quantity measured with the inclination sensor 46.

Likewise, the inclination sensor 46 may considerably contribute to saving energy in the system in that a filling level is measured, e.g., at the beginning of a tilting setting in and once the container 10, 10' has been placed down again, i.e. once the tilting has been returned from. The amount of liquid drunk may then be efficiently determined from the difference. If the inclination sensor 46 recognizes no tilting of the system, all sensors and all current consumers that are not being used may be switched off or placed into the stand-by mode so as to enable energy consumption of the socket 18 to be as low as possible.

Figure 7:
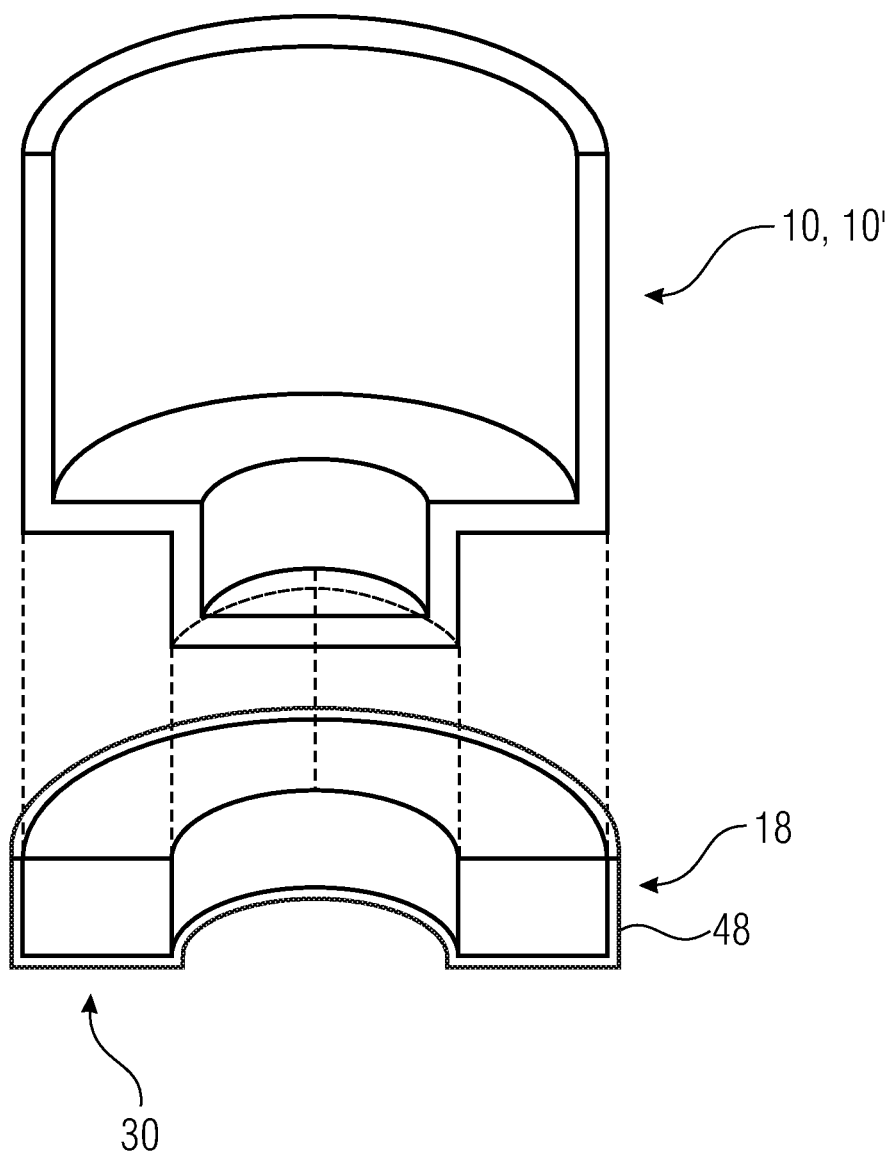
FIG. 7 shows a schematic representation of the system for coupling light into a projection of the container.

FIG. 7 shows the container 10, 10' as well as the socket 18 in accordance with a further embodiment. In accordance with this embodiment, the socket 18 comprises a casing 48 configured to protect the socket 18 from external influences, e.g. environmental influences, or to form an anti-slip bearing surface 30. This is advantageous since, in this manner, the socket 18 may be protected, for example, from any liquids that have been spilled and/or from any cleaning liquids that are employed in cleaning.

To this end, the casing 48 may include the surface area not covered by the container 10, 10', as shown in FIG. 7, or may enable complete encasing of the socket 18 (not shown).

Thus, the casing 48 may also form the fastening mechanism 38 shown with reference to FIG. 6e in that an anti-slip material in the form of the casing 48 is introduced between a connecting point of the socket 18 and the container 10, 10'.

This or any other anti-slip material may also be applied to the bottom side of the socket 18 so as to avoid slipping on a smooth surface and to enable the socket 18 and the container 10, 10' to be placed in a secure manner. The socket 18 may thus be slip-resistant, tilt-proof and/or shatter-proof.

A material for the casing 48 may comprise silicone. The casing 48, e.g. a silicone cover, may protect the floor unit, or the socket 18, from liquids, impacts and shocks. In addition, it may contribute, e.g. by analogy with known mobile phone cases, to individualizing the socket 18 in that exchangeable covers 48 having different colors, shapes or patterns are offered for sale and distributed.

In addition, there is the possibility of achieving individualization by means of, e.g., engraving, ornamentations, color, shape, material, embossing, coating of the socket (casing), clips, etc.

The substructure, or socket, 18, may be splash-proof because of the casing 48, for example, or may be protected in accordance with protection types IP55/IP57 and/or IP 67/69 and may thus also be dishwasher-safe in terms of humidity and temperature.

An engraving or a laser ornamentation within the container 10, 10' and/or in a side wall of the container 10, 10' may also reinforce prompting of the user to drink.

Thus, by specifically scattering the light into the glass 10, 10' through the socket 18 and/or the prompting means, the glass 10, 10' becoming an optical guide, engraving or lasering may be advantageous since the engraving and/or lasering results in a breaking edge within the glass 10, 10' where the light refracts (in a specific manner). Thus, by means of the light which is scattered in, specific effects may be achieved which reinforce the prompting effect, e.g. for children.

The socket 18 may further comprise a recognition mechanism which recognizes turning over or turning upside down of the socket 18 with the associated container 10, 10' and outputs a corresponding alert, e.g. in the form of (red) blinking, a vibration alert and/or an acoustic warning signal so as to signal a typically undesired condition.

Said turning upside down may occur at any angle of inclination, angles of inclination of more than 130°, more than 145°, or more than 160° being possible, by way of example.

The angle of inclination may be regarded as a rotation of the system, i.e., here, of the combination of the container 10, 10' and the socket 18, by any axis of the system, starting from a fundamental state, the fundamental state characterizing, e.g., the system placed down onto the socket 18. Thus, placing-down of the container 10, 10' in an upside-down manner in the cupboard in connection with the socket 18 may be warned against so as to prevent unnecessary discharging of the socket 18 in the connected state.

In addition, e.g. with a socket 18 that is not configured to be dishwasher-proof, a warning may be emitted against placing the container 10, 10' into the dishwasher together with the socket 18 in case the user has forgotten to remove the socket 18 prior to placing the container 10, 10' into the dishwasher. Thus, damage to the socket 18 may be prevented.

In other words, the prompting means may be configured to issue a warning signal in case an angle of inclination, which represents the system being turned upside down, is exceeded.

Figure 8:
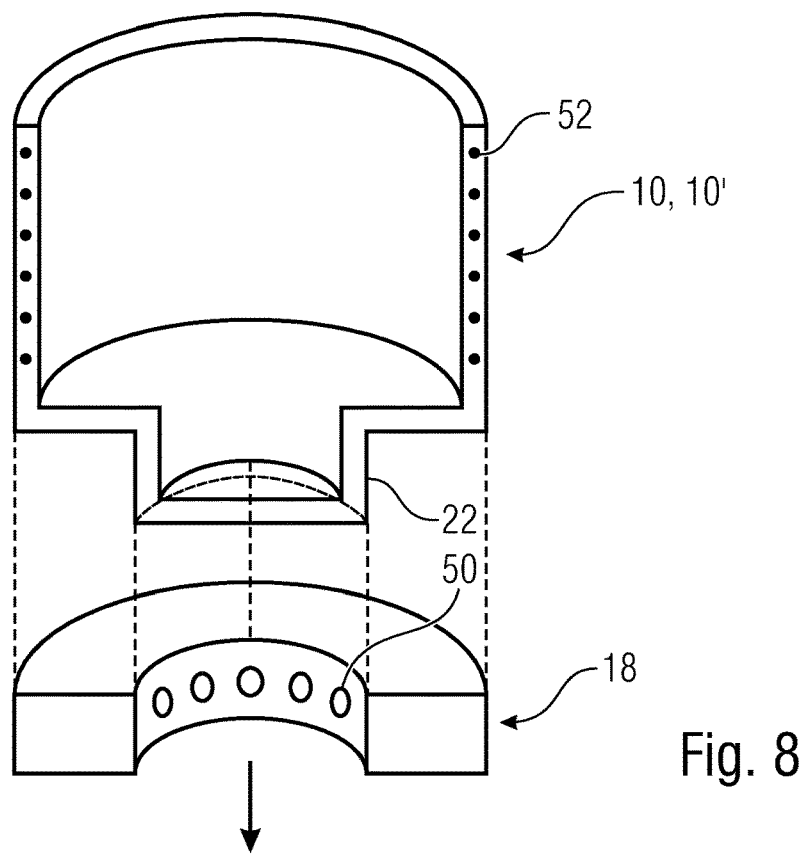
FIG. 8 is a schematic cross-sectional view of a further embodiment of the system; it is possible, irrespective of the embodiment selected, to adapt the socket to different container sizes by mounting an extension element.
Figure 9:
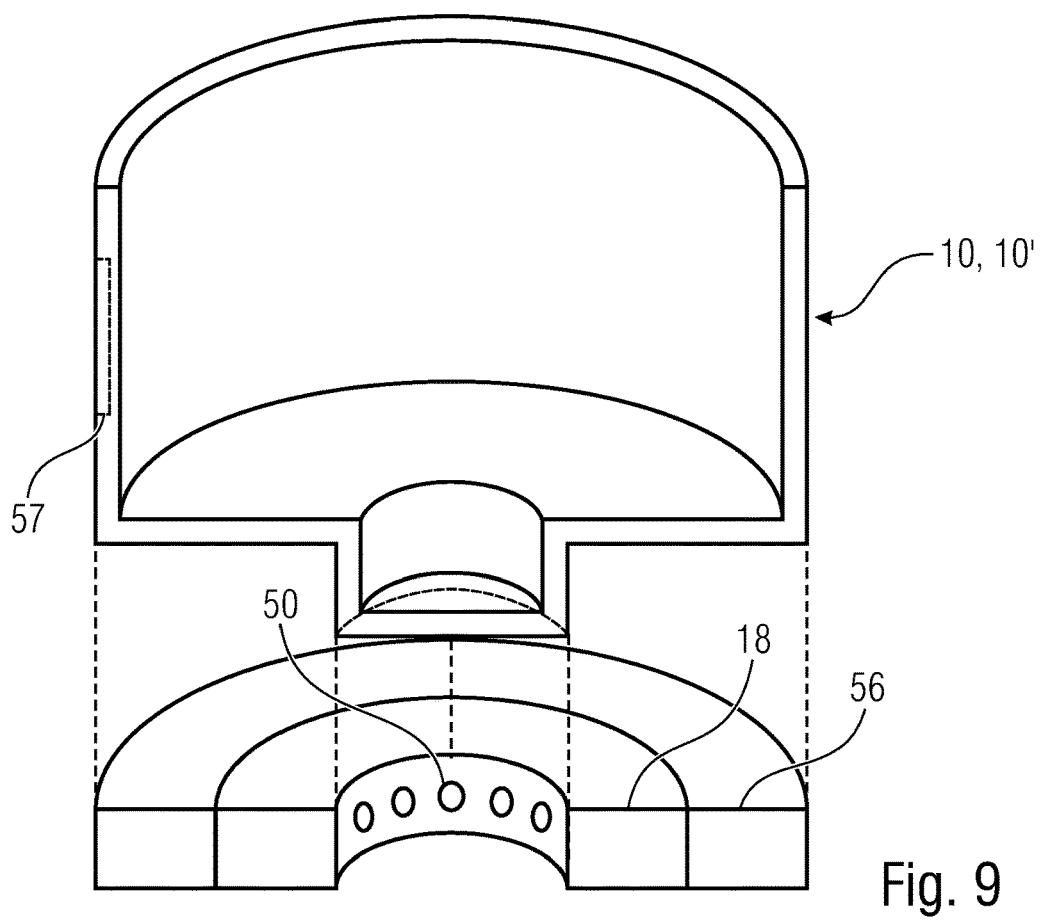
FIG. 9 shows a container of a second size as compared to FIG. 8.

FIGS. 8 and 9 show cross-sectional views of the container 10, 10' and of the socket 18 in different sizes in accordance with a further embodiment. In the embodiment shown, the container 10, 10' may be formed from a transparent material.

For prompting purposes, the evaluation unit may further couple light into the container 10, 10', e.g. via the light sources 50 within the socket 18.

Moreover, the container 10, 10' may comprise scattering centers 52 configured to scatter the light that has been coupled in.

In accordance with a further embodiment, the evaluation unit may be configured to apply, for prompting purposes, an electric voltage or an electric current to the container 10, 10' and to excite prompting means introduced into or applied onto the container 10, 10'. Said prompting means may be, for example, a motor exhibiting an unbalance—by analogy, e.g., with a vibrating alert of a mobile phone, or light emitting diodes or other illuminants introduced into the container 10, 10'.

Moreover, the container 10, 10' may have an excitable color applied to it which will luminesce or fluoresce and, therefore, emit light, upon application of an electric voltage or an electric current.

In accordance with embodiments, the evaluation unit may be configured to couple the light into the container 10, 10' at a projection 22. This is advantageous since in this manner a reduced floor space and, therefore, instability of the container 10, 10' are created by the formation of the projection 22, which reduced floor space and instability are compensated for by a recess within the socket 18 which matches the projection 22. Thus, the container 10, 10' may be placed on a surface in combination with the socket 18 without any restrictions, whereas the container 10, 10' exhibits reduced stability without the socket 18.

In other words, the container 10, 10' may be implemented with such a shape that it may be placed down for storage purposes. However, if the container 10, 10' is filled without having previously mounted a floor unit and/or the socket 18, the container 10, 10' will tend to tilt.

As shown in FIG. 9, an expansion element 56 may be arranged around the socket 18, so that also containers 10, 10' having enlarged diameters, such as bottles or carafes, may be safely placed within the socket 18. Thus, an arrangement which is low-cost since it is modular is provided for adapting the socket 18 to various container sizes with little expenditure.

In addition, embodiments show that a carafe and/or a socket 18 mounted on a carafe comprises a sensor which recognizes, e.g. in combination with the filling level sensor monitoring a container 10, 10', which container 10, 10' the liquid from the carafe is poured into, and will perform corresponding association with a person. Said value may serve as a sole reference for the amount of liquid poured or may be used, in combination with an evaluation of the filling level measurement at the container 10, 10', for optimized calculation of the amount of liquid contained within the container 10, 10', e.g. by averaging the values, or may be used for recognizing outliers and/or erroneous detections.

In accordance with a further embodiment, the container 10, 10' may comprise a hand sensor 57 configured to sense body contact with the container 10, 10'. The hand sensor 57 is configured, e.g., as a capacitive sensor or a pressure sensor which senses body contact with the container 10, 10'. For this purpose, one may use sensors 57 which are also employed in touch-sensitive screens, e.g. of smartphones.

In other words, the drinking container 10, 10' may be provided with a layer enabling sensitive capacitive touch measurement. Alternatively or additionally, the hand sensor 57 may also be arranged inside the wall of the container 10, 10', as shown in FIG. 8.

The hand sensor 57 may be used for avoiding sources of error or measuring gaps. Permanent monitoring and/or measuring of the contents of the receptacle may consume a large amount of energy. In this manner, it is to be made possible to make useful measurements when the glass 10, 10' is touched in an encompassing manner and when, therefore, intake of liquid or refilling of the glass may be expected.

Likewise, the hand sensor 57 may be used for distinguishing between deliberate and inadvertent removal of liquid since there is typically no (continuous) contact with the container 10, 10' when the container 10, 10' is knocked over by mistake. Thus, one may conclude that the liquid was removed from the container 10, 10' but not taken in, or drunk, by the user.

In accordance with further embodiments, the container 10, 10', which needs not necessarily comprise a socket 18 and may also be a plate, for example, may comprise an element for analyzing the food present on and/or within the container 10, 10'. Said element is, e.g., an electrode which analyzes the food e.g. by means of cyclic voltammetry. In addition, other, e.g. chemical or physical, methods of analysis may also be employed separately or in combination of different methods.

By determining the foods taken in, a nutrient analysis may also be performed, for example, so that the above-described prompting to take in liquids may be extended to the effect that generally, a recommendation to take in foods may be output so as to support a balanced diet of the user.

In accordance with a further embodiment, the user of the system may sense the filled-in liquid himself/herself. To this end, it is enough to scan the EAN/GTIN code (EAN: European Article Number; GTIN: Global Trade Item Number) from the beverage bottle, for example by means of the smartphone camera. A database query will determine the type of beverage at hand. Databases that may be used for this purpose are readily available. Information (nutrients, minerals, etc.) about the respective beverage may then be queried via further databases, such as www.fddb.info, for example, and may be stored in the application. Said information may be evaluated in a further step, e.g. in the analysis of a person's drinking behavior.

Via the technology contained within the substructure, or socket, 18, a quick scan, or a fast analysis, of the contents of the receptacle is initiated during sensing via the code scan described. On the one hand, this enables recurrent beverages to be immediately recognized and sensed by the system. On the other hand, the user may be prompted, by a warning message, to scan the EAN/GTIN code once again when the contents of the receptacle changes and if no change of the beverage has been made by the user in the application (e.g. a change from fruit juice to water). This results in that incorrect values are not included inadvertently in the analysis of the user's drinking behavior.

Beverages that cannot be associated with any clear EAN/GTIN code (e.g. (individually mixed) mixed drinks such as spritzers etc.) may be manually sensed within the system. However, the partial quantities of the mixed drink may be sensed when the liquids to be mixed are filled into the container 10, 10' one after the other. Thus, for example, the evaluation unit may determine the exact composition of the mixed drink by means of the known partial quantities of the liquids.

In addition, food analysis may also be employed in combination with the above-described methods of measuring the filling level and/or the amount of liquid removed. For example, the liquid contained within the container 10, 10' is analyzed so as to determine, e.g., a refractive index at the interface between the liquid and the surrounding air and to thus optimize one of the described methods which are based upon deflection of electromagnetic radiation upon entry into/or exit from the liquid (cf., e.g., FIG. 6). The refractive index may be determined, e.g., on the basis of analyzing the density of the liquid or on the basis of identifying the liquid via a predefined stored table.

Figure 10:
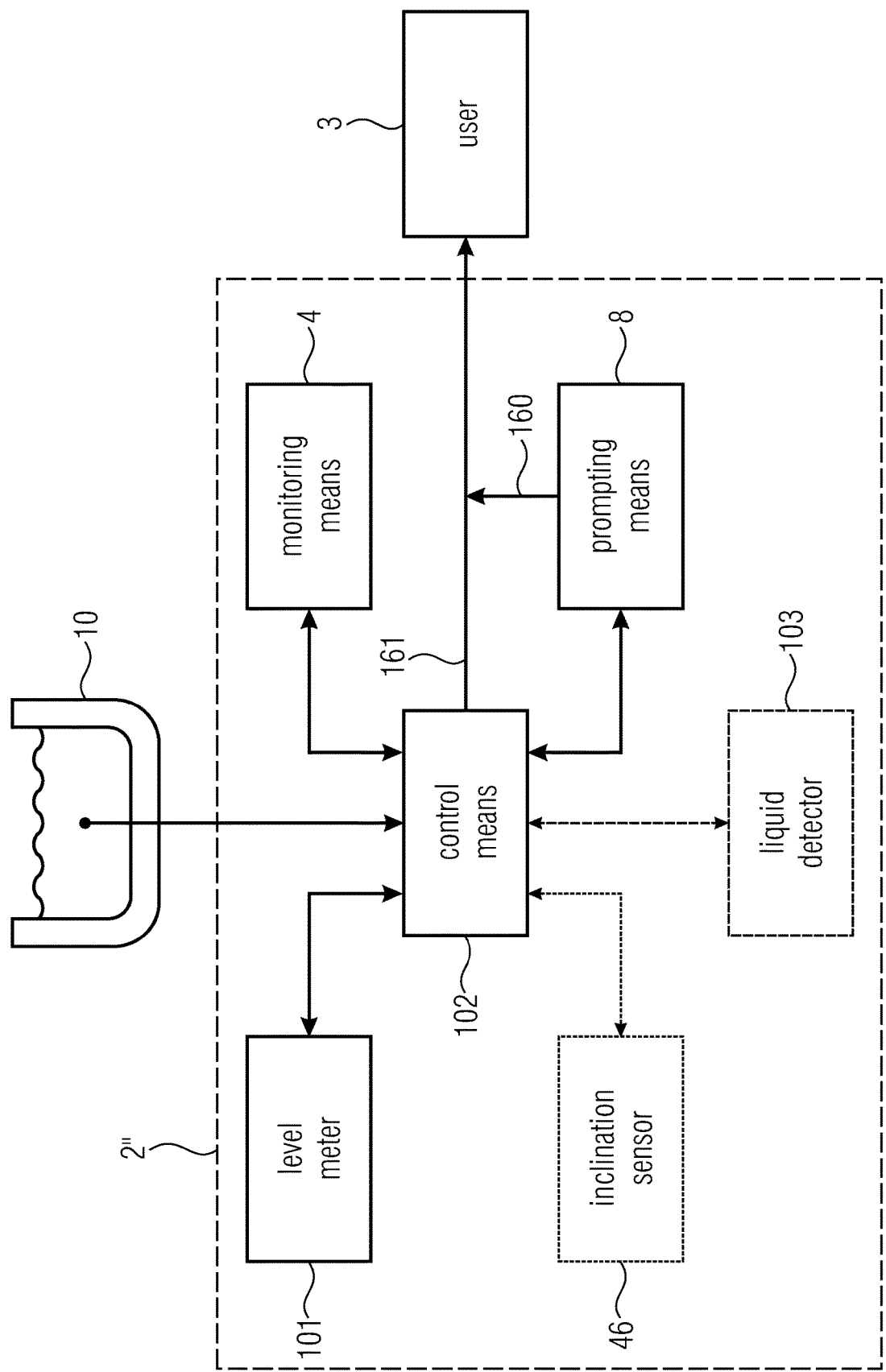
FIG. 10 shows a schematic representation of the system in accordance with an embodiment.

The filling level may be measured, for example, by means of an inventive level meter 101. For example, FIG. 10 shows an embodiment of a system 2" in accordance with a further aspect of this invention.

Among other things, the system 2" comprises a container 10 for receiving liquid. In addition, the system 2" comprises, just like the systems 2, 2' described previously, monitoring means 4 and prompting means 8.

As was previously described, the monitoring means 4 is configured, also in this embodiment, to determine an amount of liquid removed from the container 10, and the prompting means 8 is configured to prompt the user 3 to drink as a function of the amount of liquid removed.

In addition, the system 2" in accordance with this aspect comprises a level meter 101 for measuring the liquid level of the liquid contained within the container 10. Generally, the system 2" depicted in FIG. 10 may be combined with any of the previously described features of the systems 2, 2'.

As will be described in more detail below, the system 2″ may further optionally comprise a liquid detector 103, may optionally comprise an inclination sensor 46, and may optionally comprise a control means 102. Said control means 102 may be, e.g., a suitable IC (integrated circuit), FPGA or microprocessor, or microcontroller.

Figure 11:
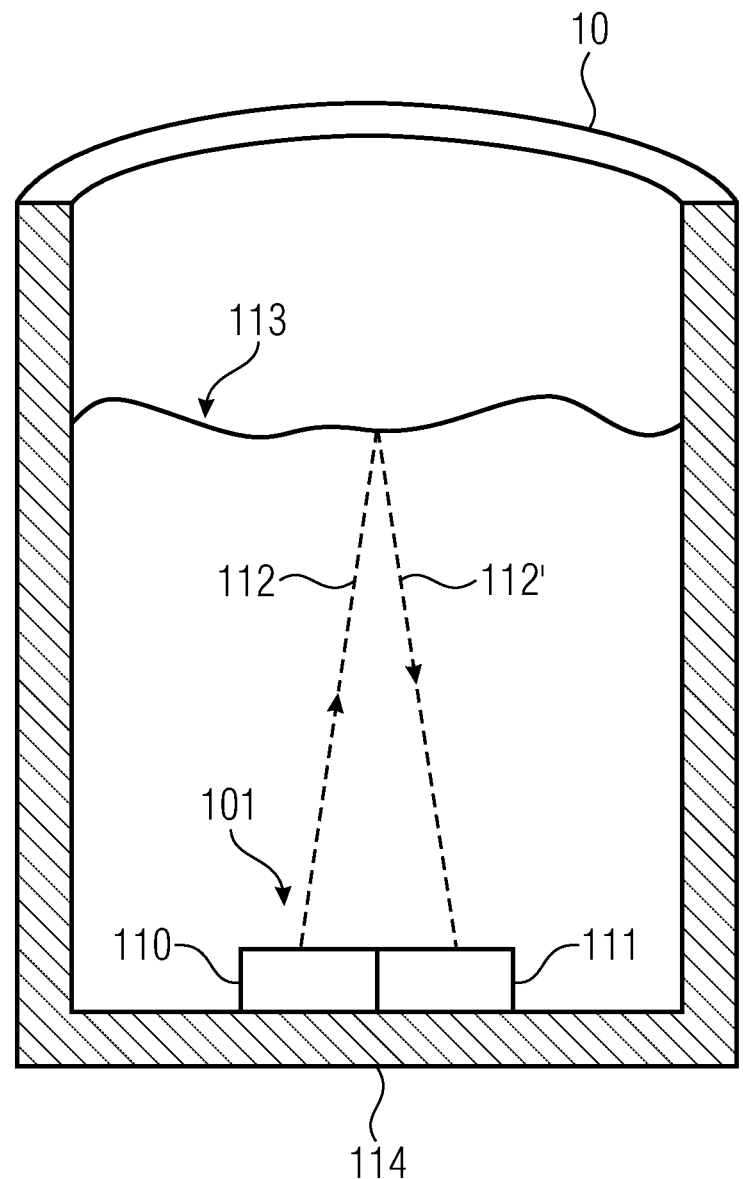
FIG. 11 shows a cross-sectional view of a container for a system in accordance with an embodiment.

FIG. 11 shows an embodiment of a container 10 for an inventive system 2″ comprising a level meter 101, the level meter 101 being an optical level meter comprising at least one emitter 110 for emitting electromagnetic radiation 112 and at least one receiver 111 for receiving the emitted electromagnetic radiation 112.

The electromagnetic radiation 112 may be, e.g., visible light within the wavelength range from 400 nm to 700 nm. However, it is also feasible that it is UV light within the wavelength range from 10 nm to 400 nm or infrared light within the wavelength range from 700 nm to 1000 nm. It would also be feasible for the electromagnetic radiation to be sound waves, e.g. ultrasound.

In accordance with an embodiment of the invention, the emitter 110 may comprise at least on laser. For example, the emitter 110 may comprise a microwave laser. Microwave lasers are also referred to as masers and may emit electromagnetic radiation within the wavelength range from 1 mm to 300 mm.

As can be seen in FIG. 11, the emitter 110 may emit the electromagnetic radiation 112 in a focused manner, e.g. in the form of a beam. With the above-mentioned lasers, this is readily possible at low cost.

In accordance with one conceivable implementation of the invention, the emitter 110 is arranged at the container 10 such that the emitted electromagnetic radiation 112 impinges upon the liquid surface 113, adjoining the surroundings, of the liquid contained within the container 10.

The receiver 111, in turn, may be arranged at the container 10 such that a portion 112′, reflected at the liquid surface 113, of the electromagnetic radiation 112 emitted by the emitter 10 may be received by the receiver 111. This is schematically shown in FIG. 11 by means of the arrow-head directions of the emitted electromagnetic radiation 112 and of the electromagnetic radiation 112′ reflected at the liquid surface 113.

As can also be seen in FIG. 11, at least one of the emitter 110 and the receiver 111 may be arranged at a container bottom 114 of the container 10. In the embodiment depicted here, both the emitter 110 and the receiver 111 are arranged at the container bottom 114, specifically on the inside of the container, i.e. in the interior of the container 10 and/or on that side of the container bottom 114 which faces the interior of the container. However, it is also feasible for at least one of the emitter 110 and the receiver 111 to be arranged on the outside of the container, at a container bottom 114 of the container 10. In this case, the emitter 110 and/or the receiver 111 would be arranged on that side of the container bottom 114 which faces away from the interior of the container 10.

Figure 13A:
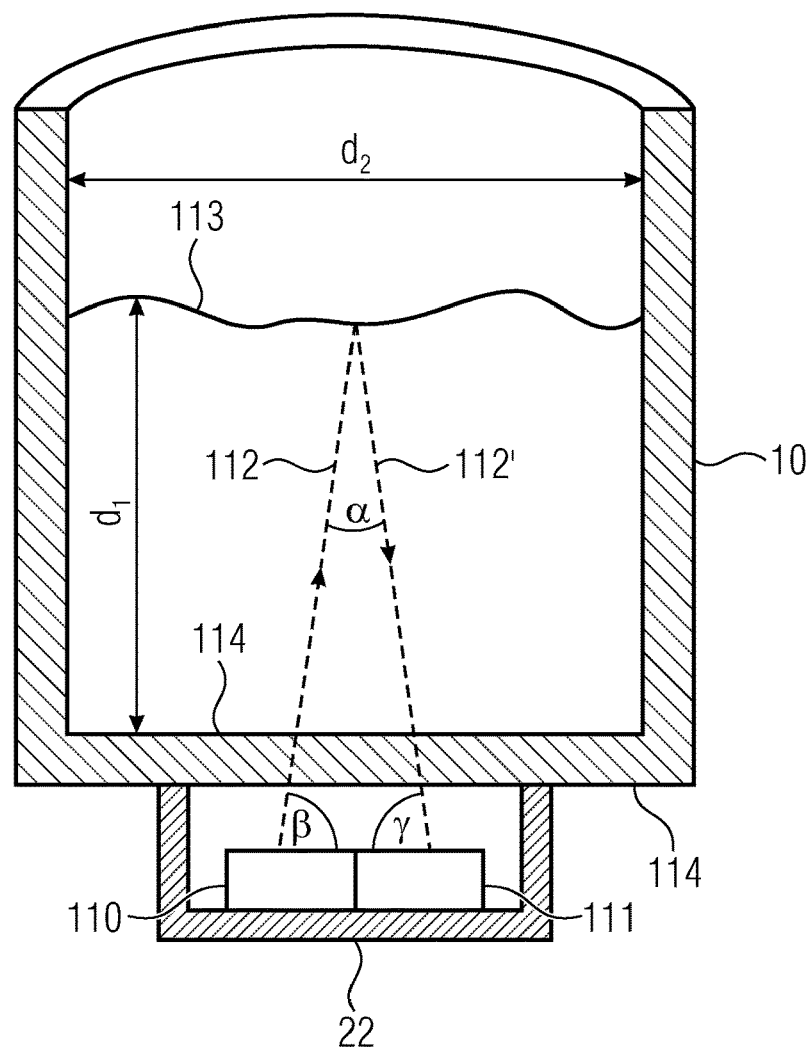
FIG. 13A is a cross-sectional view of a container for a system in accordance with a further embodiment.

Such an example is shown in FIG. 13A, among others. For example, the container 10 may comprise a projection 22 already described above. The emitter 110 and/or the receiver 111 may be arranged within said projection 22. In this case, the projection 22 may be considered as being part of the container bottom 114.

In this embodiment and in all of the ones previously described, the container bottom 114 may consist of a material that is at least partly transmissive to electromagnetic radiation 112. For example, the container bottom 114 may be made of glass (e.g., plexiglass, mineral glass).

The system 2″ may comprise one or more receivers 111. For example, such a receiver 111 may be configured as a photodiode or a light sensor. The receiver 111 may be arranged to directly adjoin the emitter 110 or to be spaced apart from the emitter 110.

Figure 12A:
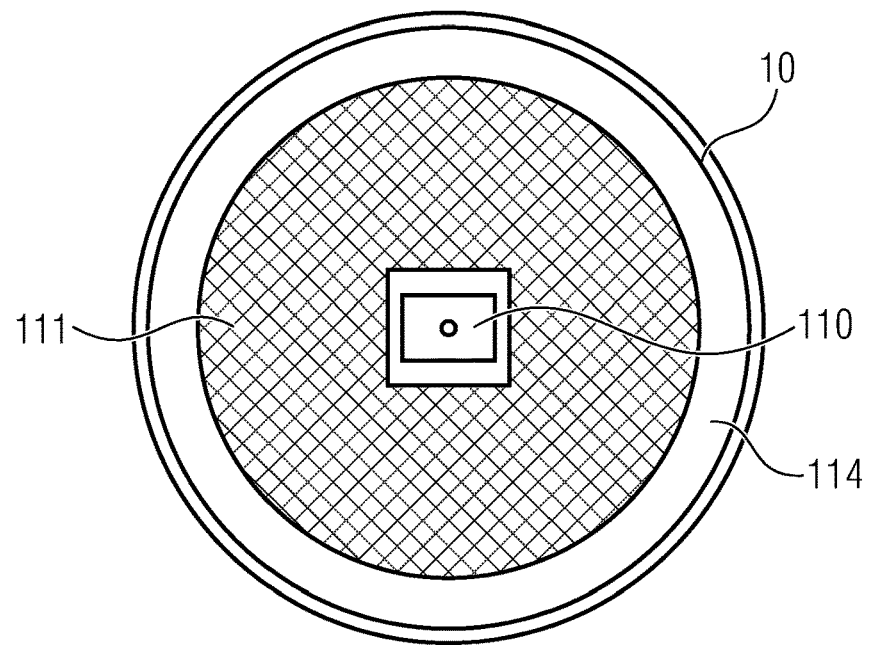
FIG. 12A shows a top view of a container for a system in accordance with an embodiment.

FIG. 12A shows an embodiment of arranging the emitter 110 and the receiver. FIG. 12A shows a top view of a container 10. Inside the container, an emitter 110 here is arranged at the container bottom 114. The emitter 110 is arranged more or less at the center of the container bottom 114.

A receiver 111 is arranged around the emitter 110. The rectangular shape of the emitter 110 and the round shape of the receiver 111 here are shown merely by way of example. Both the emitter 110 and the receiver 111 may have any geometric shapes.

Figure 12B:
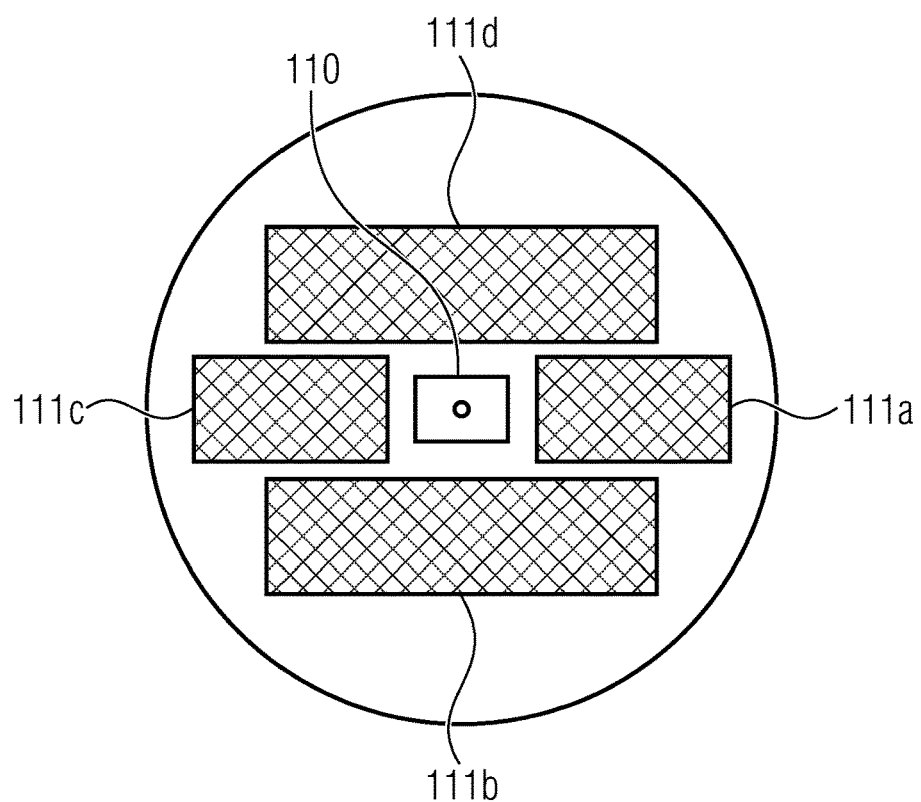
FIG. 12B shows a top view of a container for a system in accordance with a further embodiment.

As is shown in FIG. 12A, the receiver 111 may be an area sensor. However, it would also be feasible for the receiver 111 to comprise several individual point sensors. It would also be feasible for the emitter 110 to have several receivers 111*a* to 111*d* arranged around it which in turn might be interconnected in the form of an array, for example, as is depicted in FIG. 12B, for example.

As was mentioned at the outset and is shown in FIG. 13A, for example, the emitter 110 may thus be arranged at the container 10 and be oriented such that the emitted electromagnetic radiation 112 impinges upon the surface 113 of the liquid contained within the container 10. The receiver 111, in turn, may be arranged at the container 10 and be oriented such that the receiver 111 receives the electromagnetic radiation 112′ reflected at the liquid surface 113.

The emitter 110 may emit the electromagnetic radiation 112 at a specific exit angle β that is inclined to the liquid surface 113. The electromagnetic radiation 112 impinging upon the liquid surface 113 is reflected at the boundary between the liquid surface 113 and the external environment (typically air). The reflected electromagnetic radiation 112′ impinges upon the receiver 111 at a specific angle of incidence γ, the angle of incidence γ also being inclined in relation to the liquid surface 113, i.e., at an angle different from 90°.

On the liquid surface 113, a reflection angle α is formed between the emitted electromagnetic radiation 112 and the reflected electromagnetic radiation 112′. The reflection angle α, the exit angle β and the angle of incidence γ are mutually dependent in accordance with the mathematical relation α+β+γ=180°, wherein ideally (e.g., when the container 10 is located in a level (straightened) manner on a plane surface), β and γ may be assumed to be identical since in this ideal case, an equilateral triangle will form between the emitted electromagnetic radiation 112 and the reflected electromagnetic radiation 112′.

In the example depicted in FIG. 13A, the horizontal, or azimuth, location of the liquid surface 113 is roughly parallel in relation to the level sensor 101. This means that when the container is positioned to be level as depicted in FIG. 13A, the emitter 110 and the receiver 111 will be oriented in parallel with the liquid surface 113.

If in this case, the filling level $d_1$ changes but the horizontal, or azimuth, location of the liquid surface 113 does not change in relation to the level sensor 101, the angles, i.e., the reflection angle α, the exit angle β and the angle of incidence γ also remain unchanged in terms of their quantities. However, as the liquid level inside the container 10 varies, a geometric distance between a location of sending out the emitted electromagnetic radiation and a location of receiving the reflected electromagnetic radiation will change. This is to be explained, by way of example, with reference to FIG. 13B.

Figure 13B:
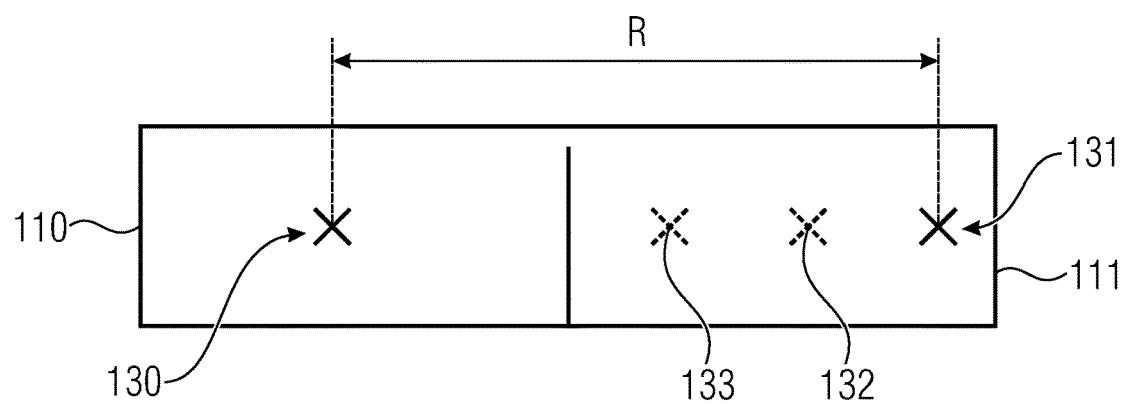
FIG. 13B shows a schematic top view of an emitter and a receiver of a level meter for a system in accordance with an embodiment.

FIG. 13B shows an enlarged schematic top view of a level meter 101 comprising an emitter 110 and a receiver 111. The cross 130 symbolizes a point of exit of the emitted electromagnetic radiation 112. The cross 131 symbolizes a point of impingement of the reflected electromagnetic radiation 112' upon the receiver 111. The point of exit 130 and the point of impingement 131 are spaced apart from each other by a measure R.

As the filling level $d_1$ within the container 10 decreases, the distance R between the exit point 130 and the point of impingement 131 is reduced. For example, in case of a second filling level that is lower than the first filling level, the point of impingement of the reflected radiation 112' would be at the second cross 132 depicted in dashed lines. And in case of a third filling level that would be even lower than the second filling level, the point of impingement of the reflected radiation 112' would be, e.g., at the third cross 133 depicted in dashed lines.

In such an embodiment, the level meter 101 might be coupled to the control means 102 (FIG. 10) which was already mentioned previously, the control means 102 being configured to determine the filling level of the liquid contained within the container 10 while taking into account a geometric distance R between a location 130 of sending out the emitted electromagnetic radiation 112 and a location 131 of receiving the reflected electromagnetic radiation 112'.

An advantage of the invention consists in that even upon a change in the azimuth location of the liquid surface 113 in relation to the emitter 110 and/or receiver 111, the filling level can be determined by means of the inventive level meter 101.

For example, FIG. 14A shows a further embodiment. The container 10 comprises, on that side of the container bottom 114 that faces the interior of the container, an emitter 110 and a receiver 111 arranged around the emitter 110.

As compared to the container 10 depicted in FIG. 13A, the container 10 is inclined, which may occur during a drinking movement, for example. As a result, the azimuth location of the liquid surface 113 in relation to the emitter 110 and/or receiver 111 changes. Consequently, the reflection angle α is larger than that depicted in FIG. 13A while the exit angle β of the emitter 110 remains unchanged. By contrast, the angle of incidence γ is smaller than in the embodiment depicted in FIG. 13A while the exit angle β of the emitter 110 remains unchanged. In addition, the point of impingement 131 of the reflected electromagnetic radiation 112' upon the receiver 111 is located further toward the outside as compared to the non-inclined container 10 depicted in FIG. 13A, i.e., the geometric distance R is larger.

While taking into account said conditions that were described above, with a suitable container 10, the control means 102 may optionally be additionally coupled to an inclination sensor 46. The inclination sensor 46 measures the inclination of the container 10 and calibrates level measurement of the liquid contained within the container 10 by a specific value corresponding to the amount of inclination of the container 10.

In accordance with such an embodiment, therefore, the control means 102 may optionally be coupled to an inclination sensor 46 measuring an inclination of the container 10, and the control means 102 may further be configured to determine the filling level of the liquid contained within the container 10 while taking into account the inclination measured.

For completeness' sake, FIG. 14B shows the container 10 in the same angular position as in FIG. 14A. However, the filling level of the liquid contained within the container 10 has dropped as compared to FIG. 14A. As was mentioned at the outset, the reflection angle α, the exit angle β and the angle of incidence γ indeed remain unchanged as the angular position of the level meter 101 (i.e., emitter 110 and/or receiver 111) remains unchanged in relation to the liquid surface 113. However, the geometric distance R between the location 130 of sending out the emitted electromagnetic radiation 112 and the location 131 of receiving the reflected electromagnetic radiation 112' does change. Accordingly, the geometric distance R is smaller in the example shown in FIG. 14B than in the example shown in FIG. 14A.

By means of the above-mentioned geometric relationships and of the possibility of correcting the level measurement, upon inclination of the container 10, by means of the inclination sensor 46, the level meter 101 can determine the filling level of the liquid contained within the container 10 both with the container 10 being oriented in a level (straightened) manner and with the container 10 being oriented in an inclined manner. This offers the advantage that the filling level of the container 10 may be measured also during a drinking action, for example.

For example, the distance $d_1$ between the liquid surface 113 and the container bottom 114 on the inside of the container may be determined via the relationships of the exit angle α, the reflection angle β and the angle of incidence γ as well as on the basis of the knowledge of the geometric distance R between the exit point 130 and the point of impingement 131, of the inclination of the container 10 and of the volume $V_{container}$ of the container 10. Said distance $d_1$ corresponds to the current filling level.

For example, with a container 10 which is located in a level manner, the filling level of the container 10 may be calculated on the basis of the knowledge of the volume $V_{container}$ of the container 10. For example, if the container 10 is a circular cylinder, as depicted in FIG. 13A, the filling level $d_1$ may be calculated, e.g., in accordance with the following formula:

$$V_{container} = \pi \cdot \left(\frac{d_2}{2}\right)^2 \cdot d_1$$

If at least one of the angles, i.e., exit angle β, reflection angle α and angle of incidence γ, as well as the geometric distance R have been determined, or are known, the filling level $d_1$ may also be determined as follows by means of the angular relationships:

$$d_1 = \tan \gamma \cdot R$$

Alternatively or additionally, the level meter 101 may determine the filling level of the liquid contained within the container 10 also by means of run-time measurement. To this end, the level meter 101 may be coupled to the previously mentioned control means 102 configured to determine the filling level of the liquid contained within the container 10 while taking into account a run-time measurement of the electromagnetic radiation 112 between the emitter 110 and the receiver 111.

Here, the run time of the electromagnetic radiation 112 emitted by the emitter 110 up to the impingement of the reflected electromagnetic radiation 112' upon the receiver is measured. The lower the liquid level within the container 10, the shorter the run time measured will be since the emitted electromagnetic radiation is reflected at the liquid surface 13 at an earlier point in time. The control means 102 here is configured to calculate the filling level by means of the run time measured.

The above-described inventive systems 2, 2', 2'' may also comprise a liquid detector 103. One may ascertain by means of the liquid detector 103 whether or not there is liquid contained within the container 10. If no liquid is detected within the container 10, one may conclude, e.g., that the container 10 currently (e.g., at night time) is not in use. Electronic components may then be switched to a standby mode.

Figure 15B:
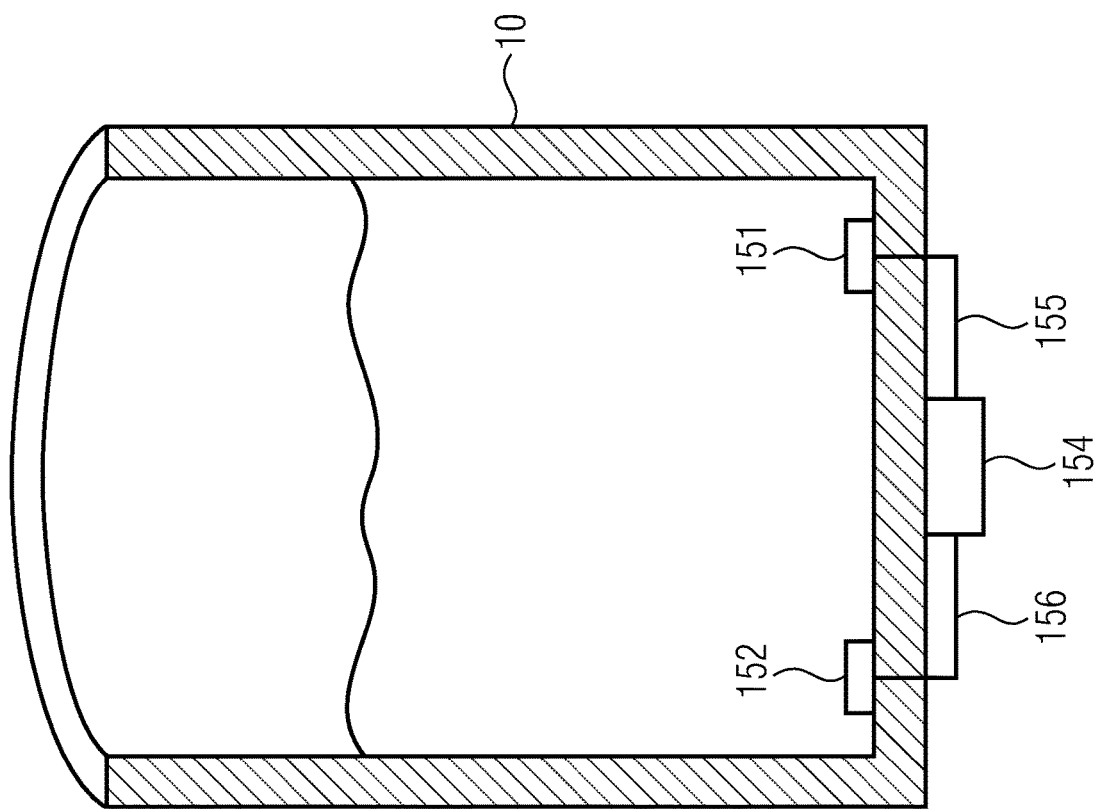
FIG. 15B shows a cross-sectional view of a container comprising a liquid detector for a system in accordance with a further embodiment.
Figure 15A:
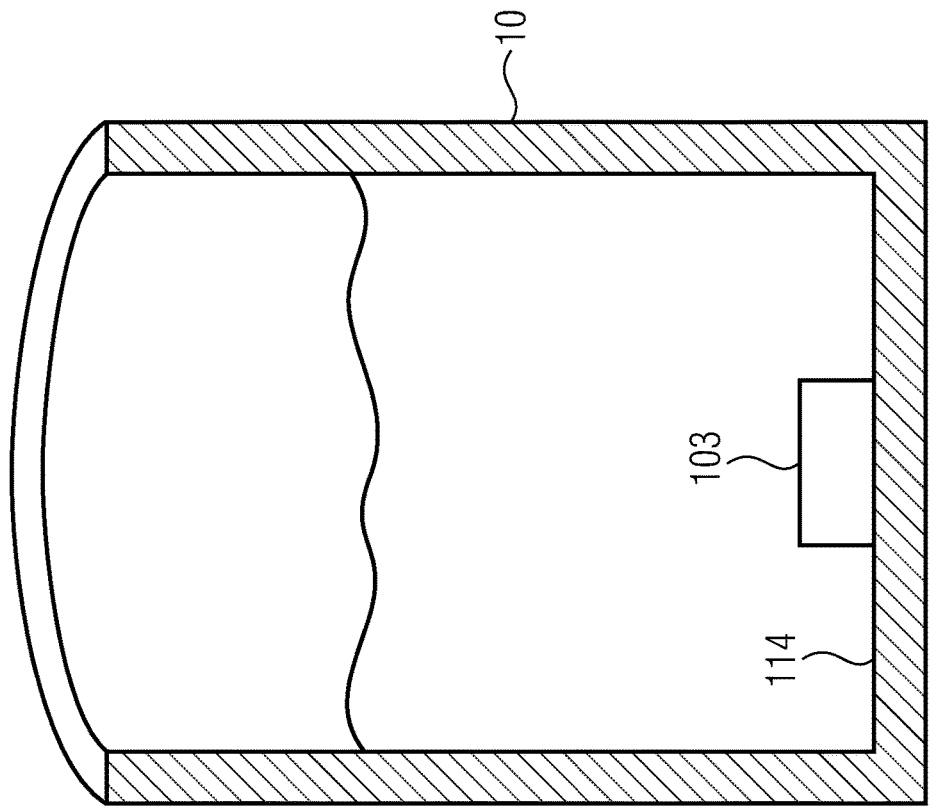
FIG. 15A shows a cross-sectional view of a container comprising a liquid detector for a system in accordance with an embodiment.

FIG. 15A shows an embodiment of such a system comprising a container 10, the container 10 comprising a liquid detector 103 configured to detect whether or not there is liquid contained within the container 10. As can be seen in FIG. 15A, the liquid detector 103 may be in contact, at least in some portions, with a liquid to be detected inside the container 10.

For example, the liquid detector 103 may be arranged at the container bottom 114. In this context, the liquid detector 103 may be arranged, for example, on that side of the container bottom 114 which faces the interior of the container, as shown in FIG. 15A. In this case, the liquid detector 103 is in direct contact with the liquid contained within the container 10.

FIG. 15B shows a further embodiment of a liquid detector 103. Here, the liquid detector 103 comprises a first electric contact 151 and a second electric contact 152. Both electric contacts 151, 152 are arranged at a distance from each other. The electric contacts 151, 152 are configured such that an electric circuit between said two contacts 151, 152 may be closed by means of the liquid to be detected within the container 10.

For example, the first electric contact 151 is connected to a signal circuit 154 via an electric lead 165. The second electric contact 152 is also connected to the signal circuit 154 via a further electric lead 155. Both electric contacts 151, 152 may be brought into contact, at least in some portions, with the liquid to be detected within the container 10. In this example, both electric contacts 151, 152 are arranged on that side of the container bottom 114 which faces the interior of the container.

If there is no liquid contained within the container 10, the electric contacts 151, 152 are not closed. No current flows through the signal circuit 154. Only when there is liquid contained within the container 10, the electric circuit between both electric contacts 151, 152 is closed by means of said liquid. Thus, current flows through the signal circuit 154, as a result of which the presence of liquid within the container 10 may be detected.

Figure 15C:
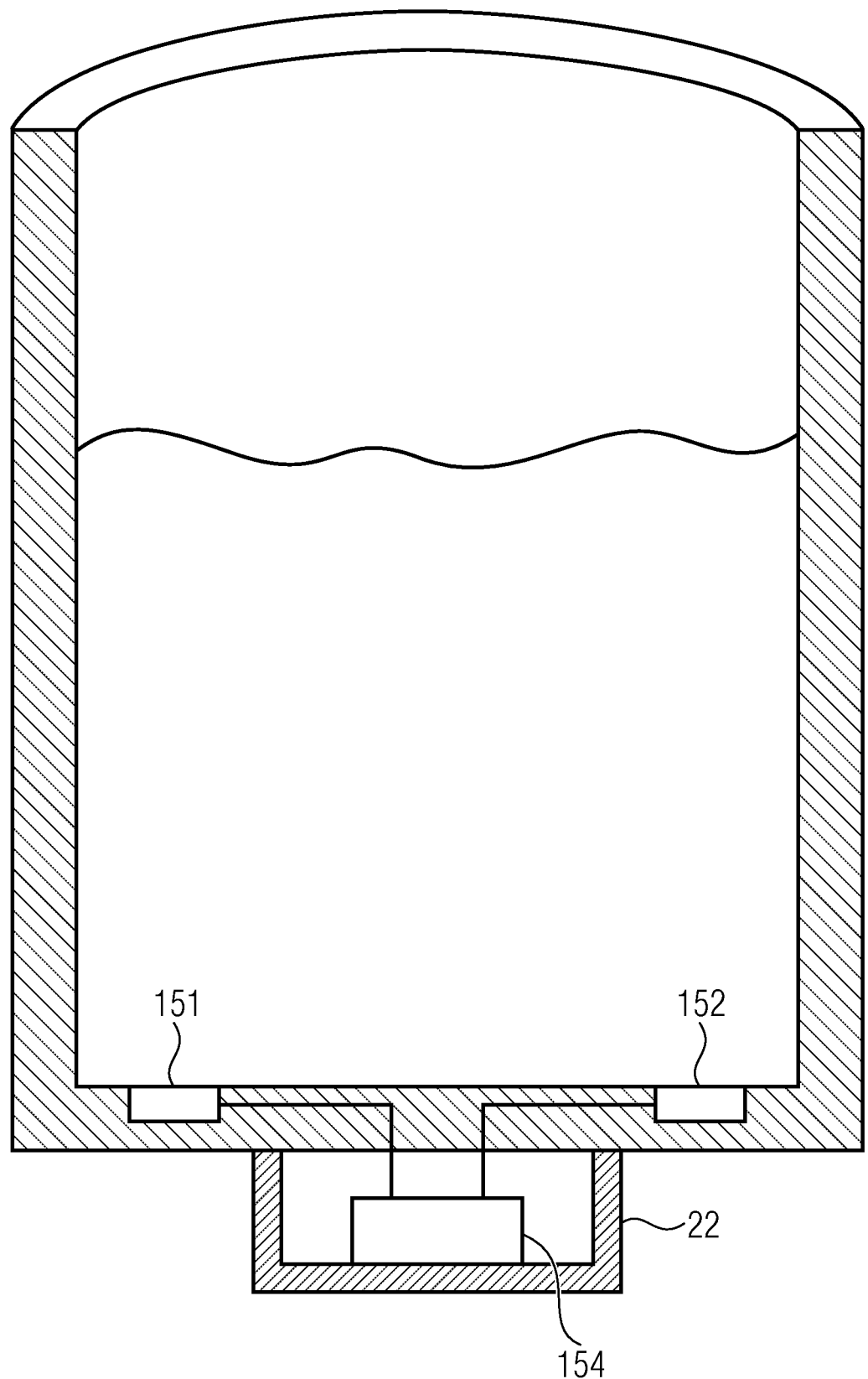
FIG. 15C shows a cross-sectional view of a container comprising a liquid detector for a system in accordance with a further embodiment.

In accordance with an embodiment, the liquid detector 103 may be integrated within the container bottom 114. Such an arrangement is shown in FIG. 15C. Here, the container 10 comprises, as part of the container bottom 114, a projection 22 which was already described in detail above. The signal circuit 154 may be integrated within the projection 22, for example.

Alternatively or additionally, at least one of the two electric contacts 151, 152 may be integrated within the container bottom 114, and in particular within that side of the container bottom 114 which faces the interior of the container. The integrated electric contacts 151, 152 may be flush with the container bottom 114, for example.

As is depicted, both electric contacts 151, 152 may be coupled to the signal circuit 154. The signal circuit 154 may in turn be coupled to the control means 102. However, the signal circuit 154 may also be part of the control means 102.

With repeated reference to FIG. 10, the inventive system 2'' thus may comprise a control means 102. The above-described level meter 101, the monitoring means 4, the prompting means 8 and, optionally, an inclination sensor 46 and a liquid detector 103 may in turn be coupled to said control means 102. The control means 102 may take over control of the level meter 101 and/or of the liquid detector 103 and may calculate the above-described level measurement and/or liquid detection.

The control means 102 itself may in turn be coupled to the container 10 or to the above-described socket 18.

Communication between the control means 102 and the level meter 101, the monitoring means 4, the prompting means 8, the inclination sensor 46 and the liquid detector 103 may be bidirectional. The control means 102 may also receive signals from the respective elements 101, 4, 8, 46, 103 and/or may send signals to said elements.

The prompting means 8 may either interact directly with the user 3, as depicted by transition 160, or the prompting means 8 may interact with the user 3 by means of the control means 102, as depicted by transition 161.

The system 2, 2', 2'' shown may be employed, e.g., in old people's homes so as to support elderly people who are already demented, for example, to take in enough liquid per day. In addition, companies may make the system available to their employees so as to prevent diseases that may be caused by insufficient intake of liquid, and so as to consequently have employers who perform better. Likewise, the system may become a lifestyle product in the future.

Further embodiments are as follows:
All essential measurement/information and signaling functions should or may be accommodated within the base station/socket 18.
The receptacle/container 10, 10' may comprise integrated technology.
Reminding function by means of light, sound and vibration (optical, acoustic, haptic, etc.) at the base 18 with transmission to a connected receptacle 10, 10' and peripheral devices (smart bracelet, smart watch, etc.).
Reminding function may be performed via the receptacle/container 10, 10' itself.
Measuring function for filling level/weight (recognition of the receptacle 10, 10' and its net weight, measuring the amount of liquid removed for monitoring the amount of liquid to be drunk daily/the minimum amount for an individual).
Storing the data inside the base/socket 18 and synchronizing it with peripheral devices.
Data transmission/synchronization (Bluetooth, RFID, NFC and/or other contact-less technologies).
Energy supply (self-sufficient, e.g. solar, energy harvesting, momentum generator, etc.).
Coupling with, e.g., smart bracelet/smart watch and similar health and vitality analysis devices (as well as any body sensors which are used, e.g., in a smart bracelet/smart watch and similar monitoring devices, for monitoring the vital functions, transmitting information regarding the target/actual quantities, programing of functions and individual parameters via apps and/or in a web-based manner via various devices such as PC, tablet, smartphone, etc.).
Measuring dehydration by means of sensors (possibly for early detection).
Temperature monitoring (protection of electronics, and warning function with hot beverages, etc.).

Charging the storage battery by means of RFID/NFC.

USB connection as a charging function, e.g. with deep depletion of the energy store and programing interface, etc.

Utilizing the USB connection for cooling/keeping-warm function (via Peltier element, infrared, induction or the like).

Base 18 with coupling to mutually tuned receptacles 10, 10' that are in conformity with the system (mugs, bottle or receptacles such as carafes, etc., with a relatively large bottom diameter with additional adapter rings for stability, etc.) e.g. by means of positive or non-positive connection (bayonet, magnet, thread, suction pad, or similar).

Deactivating the system by place-down function (placing "upside down" etc.) to save energy, e.g. once a warning signal has been emitted, e.g. by means of red blinking, so as to avoid damage occurring in a dishwasher, for example.

Deactivating the system when the socket 18 is separated from the receptacle 10, 10', or activation upon connection with the receptacle 10, 10' (stand-by).

Coupling and recognizing various possibly personalized/encoded receptacles 10, 10'.

Personalizing the socket 18 and receptacles 10, 10' (pairing), receptacle 10, 10', possibly by means of chip, RFID, bar/IQ code, etc.

Detecting and analyzing the contents of the receptacle (nutrient/mineral-matter content, calories, etc.).

Read-out station for reading out the data via hand-held or stationary technology (possibly in combination with reading out a charge of the storage battery by means of RFID/NFC) with association with persons within databases.

Figure 16:
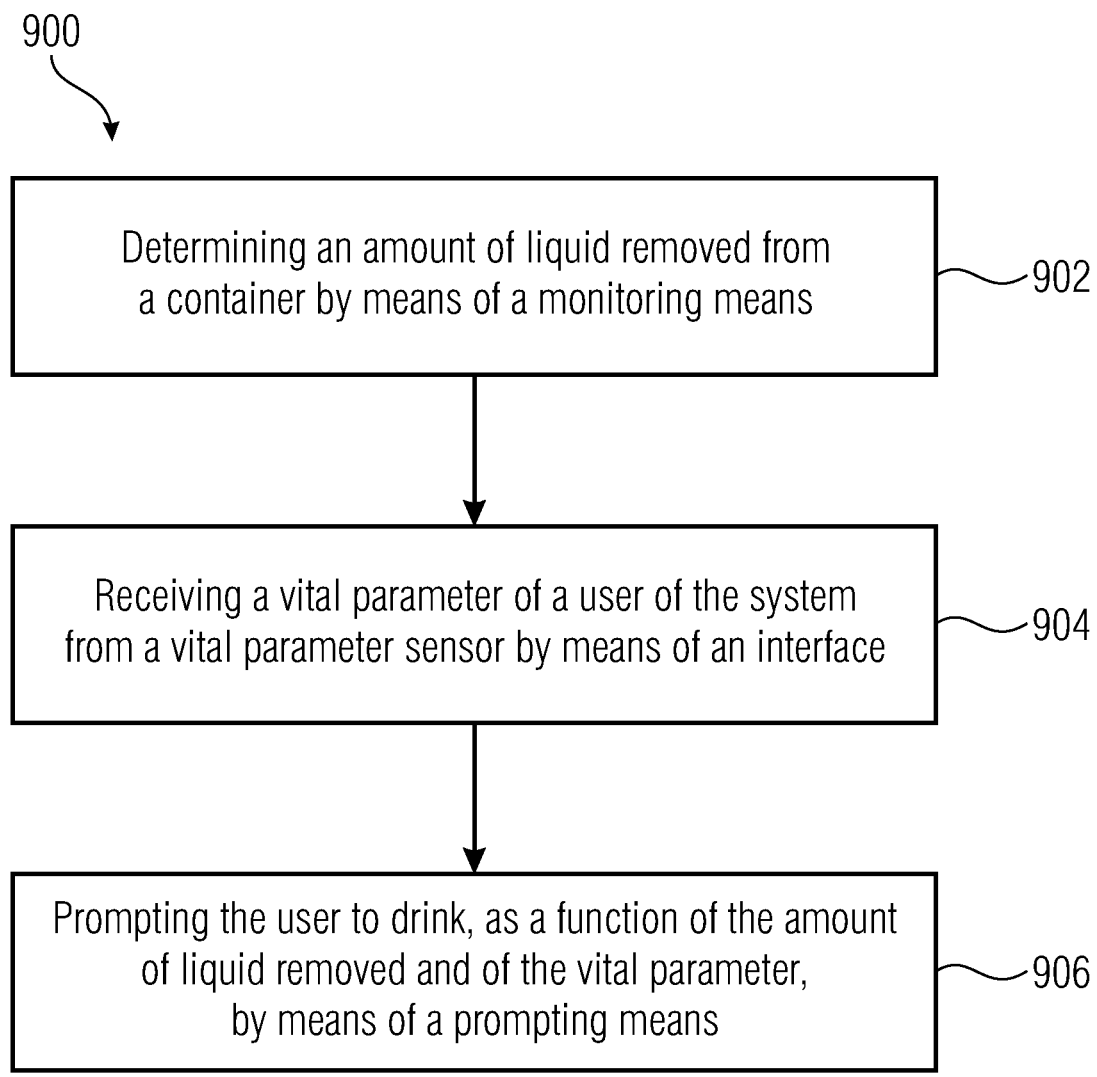
FIG. 16 shows a flowchart of a method of operating a system for monitoring liquid intake of a user in accordance with a first aspect.

FIG. 16 shows a schematic representation of a method 900 for operating a system for monitoring liquid intake of a user. The method 100 comprises a step 902 of determining an amount of liquid removed from a container 10, 10' by means of a monitoring means 4, a step 904 of receiving a vital parameter of a user system from a vital parameter sensor by means of an interface, as well as a step 906 of prompting the user to drink as a function of the amount of liquid removed and of the vital parameter, by means of a prompting means 8.

Figure 17:
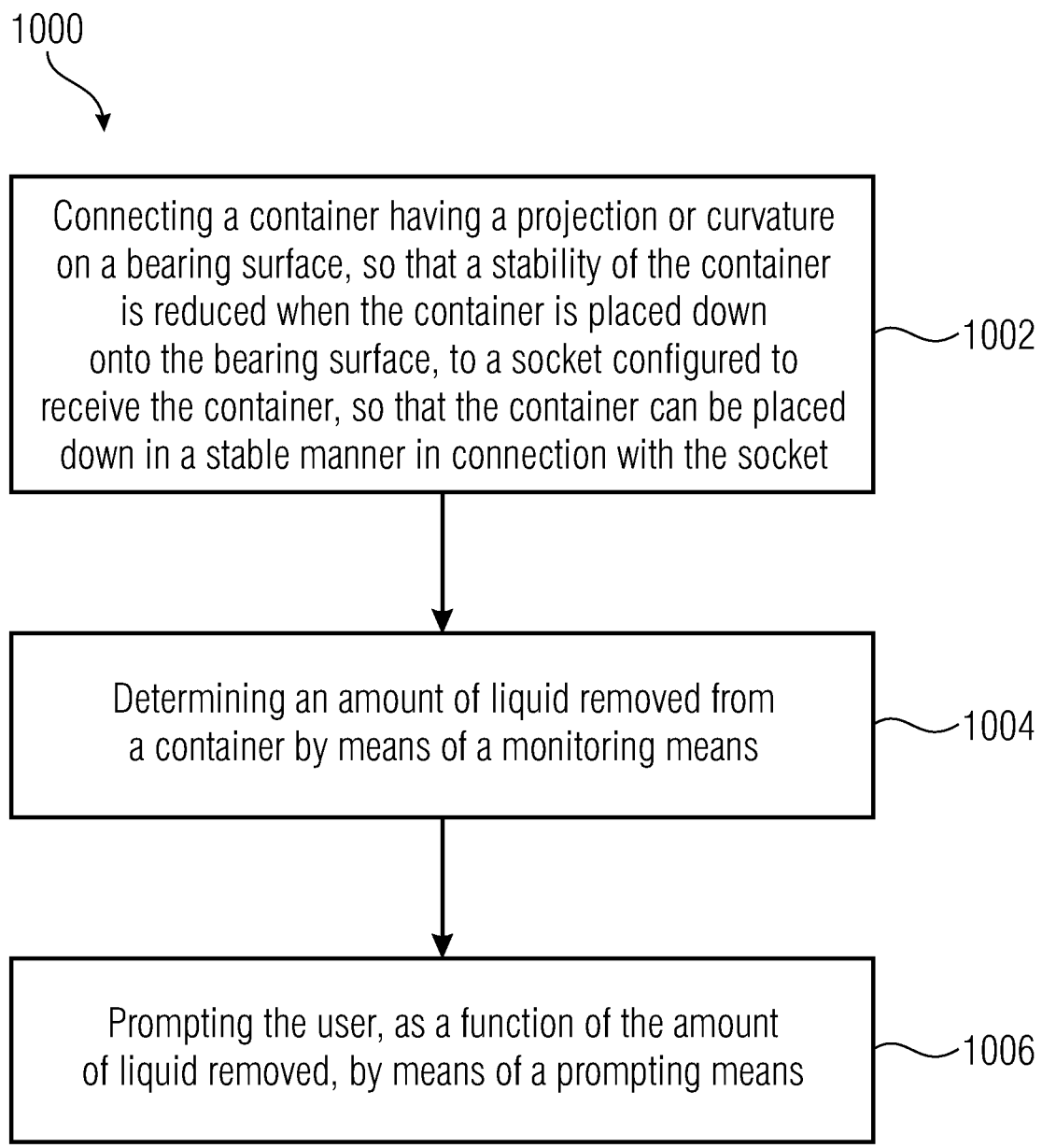
FIG. 17 shows a flowchart of a method of operating a system for monitoring liquid intake of a user in accordance with a second aspect.

FIG. 17 shows a schematic block diagram of a method 1000 of operating a system for monitoring liquid intake of a user. The system 1000 includes a step 1002 of connecting a container 10, 10' having a projection 22 or a curvature on a bearing surface, so that a stability of the container 10, 10' is reduced when the container 10, 10' is placed down onto the bearing surface, to a socket 18 configured to receive the container 10, 10', so that the container 10, 10' can be placed down in a stable manner in connection with the socket 18, a step 1004 of determining an amount of liquid removed from the container 10, 10' by means of a monitoring means 4, as well as a step 1006 of prompting the user, as a function of the amount of liquid removed, by means of a prompting means 8.

Even though some aspects have been described within the context of a device, it is understood that said aspects also represent a description of the corresponding method, so that a block or a structural component of a device is also to be understood as a corresponding method step or as a feature of a method step. By analogy therewith, aspects that have been described within the context of or as a method step also represent a description of a corresponding block or detail or feature of a corresponding device. Some or all of the method steps may be performed by a hardware device (or while using a hardware device), such as a microprocessor, a programmable computer or an electronic circuit. In some embodiments, some or several of the most important method steps may be performed by such a device.

Depending on specific implementation requirements, embodiments of the invention may be implemented in hardware or in software. Implementation may be effected while using a digital storage medium, for example a floppy disc, a DVD, a Blu-ray disc, a CD, a ROM, a PROM, an EPROM, an EEPROM or a FLASH memory, a hard disc or any other magnetic or optical memory which has electronically readable control signals stored thereon which may cooperate, or actually do cooperate, with a programmable computer system such that the respective method is performed. This is why the digital storage medium may be computer-readable.

Some embodiments in accordance with the invention thus comprise a data carrier which comprises electronically readable control signals that are capable of cooperating with a programmable computer system such that any of the methods described herein is performed.

Generally, embodiments of the present invention may be implemented as a computer program product having a program code, the program code being effective to perform any of the methods when the computer program product runs on a computer.

The program code may also be stored on a machine-readable carrier, for example.

Other embodiments include the computer program for performing any of the methods described herein, said computer program being stored on a machine-readable carrier. In other words, an embodiment of the inventive method thus is a computer program which has a program code for performing any of the methods described herein, when the computer program runs on a computer.

A further embodiment of the inventive methods thus is a data carrier (or a digital storage medium or a computer-readable medium) on which the computer program for performing any of the methods described herein is recorded.

A further embodiment of the inventive method thus is a data stream or a sequence of signals representing the computer program for performing any of the methods described herein. The data stream or the sequence of signals may be configured, for example, to be transferred via a data communication link, for example via the internet.

A further embodiment includes a processing means, for example a computer or a programmable logic device, configured or adapted to perform any of the methods described herein.

A further embodiment includes a computer on which the computer program for performing any of the methods described herein is installed.

A further embodiment in accordance with the invention includes a device or a system configured to transmit a computer program for performing at least one of the methods described herein to a receiver. The transmission may be electronic or optical, for example. The receiver may be a computer, a mobile device, a memory device or a similar device, for example. The device or the system may include a file server for transmitting the computer program to the receiver, for example.

In some embodiments, a programmable logic device (for example a field-programmable gate array, an FPGA) may be used for performing some or all of the functionalities of the methods described herein. In some embodiments, a field-programmable gate array may cooperate with a microprocessor to perform any of the methods described herein. Generally, the methods are performed, in some embodiments, by any hardware device. Said hardware device may be any universally applicable hardware such as a computer processor (CPU), or may be a hardware specific to the method, such as an ASIC.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. System for monitoring liquid intake of a user, comprising:
   a container,
   a vital parameter sensor,
   a monitor configured to determine an amount of liquid removed from the container;
   an interface configured to receive, from the vital parameter sensor, a vital parameter of the user of the system; and
   a prompter configured to prompt the user to drink as a function of the amount of liquid removed and of the vital parameter,
   wherein the monitor, the interface and the prompter are arranged within a socket configured to receive the container,
   wherein the container is formed of a transparent material, wherein the prompter is configured to couple light into the container for prompting, and wherein the container comprises scattering centers configured to scatter the light coupled in, and
   wherein the container comprises a projection formed in the container bottom, and wherein the prompter is configured to couple the light into the container at the projection.

2. System as claimed in claim 1, wherein the light is coupled into the projection perpendicularly to a viewing direction of a user looking into the container.

3. System as claimed in claim 1, wherein the monitor comprises a sensor configured to determine a current filling level of the container, the monitor being configured to determine the amount of liquid removed from the container by means of a time sequence of current filling levels of the container which have been determined.

4. System as claimed in claim 1, wherein the monitor is configured to determine the amount of liquid removed from the container by means of capacitive measurement, by means of optical measurement, by means of ultrasound, by means of radar, by means of a change in weight, by means of a run-time measurement, and/or by means of a conductivity measurement.

5. System as claimed in claim 1, wherein the prompter is configured to prompt the container, the vital parameter sensor or a mobile device to prompt the user to drink in a visual, auditive or tactile manner.

6. System as claimed in claim 1, wherein the prompter is arranged inside a mobile device.

7. System as claimed in claim 1, wherein the socket comprises a fastening mechanism configured to firmly connect the container to the socket in a mechanical or magnetic manner in an operating state.

8. System as claimed in claim 1, wherein the socket comprises a detection unit configured to identify the container in an operating state and to distinguish it from further containers each exhibiting a specific filling level, the distinction by the detection unit enabling determining of a container-specific amount of liquid removed and associating the container with the respective user.

9. System as claimed in claim 1, wherein the socket is configured to sense and set a temperature of the liquid comprised by the container.

10. System as claimed in claim 1, wherein the socket comprises a casing configured to protect the socket from external influences or to form an anti-slip bearing surface.

11. System as claimed in claim 1, the system comprising an energy supply unit configured to supply the system with energy in a self-sufficient manner by means of solar, by means of energy recovery, by means of a generator and/or by means of a momentum generator.

12. System as claimed in claim 1, wherein the socket comprises an inclination sensor configured to sense an inclination angle of the container.

13. System as claimed in claim 12, wherein the prompter is configured to output a warning signal when an angle of inclination, which represents that the system is being placed upside down, is exceeded.

14. System as claimed in claim 1, wherein the container comprises a hand sensor configured to sense physical contact with the container.

15. System as claimed in claim 1, comprising a drinking aid, the drinking aid being configured to determine an amount of liquid flowing through which has been removed from the container by means of the drinking aid, and to provide the amount of liquid removed from the container by means of the drinking aid to the monitor.

16. System as claimed in claim 1, wherein the container comprises a liquid detector configured to detect whether or not there is liquid comprised by the container, which liquid detector may be brought into contact, at least in some portions, with a liquid to be detected within the container.

17. System as claimed in claim 16, wherein the liquid detector comprises at least two electric contacts spaced apart from each other and configured such that an electric circuit between said two contacts may be closed by means of the liquid to be detected within the container.

18. System as claimed in claim 16, wherein the liquid detector is integrated into a container bottom of the container.

19. System for monitoring liquid intake of a user, comprising:
   a container exhibiting a projection or a curvature on a bearing surface, said projection or curvature being formed as a part of the container bottom, so that stability of the container is reduced when the container is placed down onto the bearing surface;
   a socket configured to receive the container so that the container can be placed down in a stable manner in connection with the socket;
   a monitor configured to determine an amount of liquid removed from the container; and
   a prompter configured to prompt the user to drink as a function of the amount of liquid removed,
   wherein the monitor and the prompter are arranged within the socket.

20. System as claimed in claim 19, comprising an interface configured to receive a vital parameter of the user from a vital parameter sensor, wherein the prompter is configured to prompt the user to drink as a function of the amount of liquid removed and of the vital parameter.

21. System as claimed in claim 19, the container being formed of a transparent material, the prompter being configured to couple light into the container for prompting, and the container comprising scattering centers configured to scatter the light coupled in; or
wherein the prompter is configured to apply, for prompting, an electric voltage or an electric current to the container and to excite prompters introduced into the container or applied onto the container.

22. System as claimed in claim 21, wherein the container comprises a projection, and wherein the evaluation unit is configured to couple the light at the projection into the container.

23. System for monitoring liquid intake of a user, comprising:
a container for receiving liquid;
a level meter for measuring the filling level of the liquid comprised by the container, wherein the level meter is an optical level meter comprising at least one emitter for emitting electromagnetic radiation and at least one receiver for receiving the emitted electromagnetic radiation;
a monitor configured to determine an amount of liquid removed from the container; and
a prompter configured to prompt the user to drink as a function of the amount of liquid removed,
wherein the emitter is arranged at the container such that the emitted electromagnetic radiation impinges upon the liquid surface, adjoining the surroundings, of the liquid comprised by the container,
wherein the receiver is arranged at the container such that a portion, reflected at the liquid surface, of the electromagnetic radiation emitted by the emitter is receivable by the receiver; and
wherein at least one of the emitter and the receiver is arranged at a container bottom of the container.

24. System as claimed in claim 23, wherein the emitter comprises at least one laser.

25. System as claimed in claim 23, wherein the level meter is coupled to a controller configured to determine the filling level of the liquid comprised by the container while taking into account a run-time measurement of the electromagnetic radiation between the emitter and the receiver.

26. System as claimed in claim 25, wherein the controller is coupled to an inclination sensor measuring an inclination of the container, and wherein the controller is further configured to determine the filling level of the liquid comprised by the container while taking into account the inclination measured.

27. System as claimed in claim 23, wherein the level meter is coupled to a controller configured to determine the filling level of the liquid comprised by the container while taking into account a geometric distance R between a location of sending out the emitted electromagnetic radiation and a location of receiving the electromagnetic radiation.

28. Method of operating a system for monitoring liquid intake of a user, the method comprising:
determining an amount of liquid removed from a container by means of a monitor, said container being formed of a transparent material;
receiving a vital parameter of a user of the system from a vital parameter sensor by means of an interface;
prompting the user to drink, as a function of the amount of liquid removed and of the vital parameter, by means of a prompter, and
coupling light into the container for prompting, the container comprising a projection formed in the container bottom, wherein the light is coupled into the container at the projection, and the container comprising scattering centers configured to scatter the light coupled in.

29. Method of operating a system for monitoring liquid intake of a user, said method comprising:
connecting a container comprising a projection or a curvature on a bearing surface, said projection or curvature being formed as a part of the container bottom, so that stability of the container is reduced when the container is placed down onto the bearing surface, to a socket configured to receive the container, so that the container can be placed down in a stable manner in connection with the socket;
determining an amount of liquid removed from the container by means of a monitor; and
prompting the user, as a function of the amount of liquid removed, by means of a prompter, wherein the monitor and the prompter are arranged within the socket.

30. A non-transitory digital storage medium having a computer program stored thereon to perform the method of operating a system for monitoring liquid intake of a user, said method comprising:
determining an amount of liquid removed from a container by means of a monitor, said container being formed of a transparent material;
receiving a vital parameter of a user of the system from a vital parameter sensor by means of an interface;
prompting the user to drink, as a function of the amount of liquid removed and of the vital parameter, by means of a prompter, and
coupling light into the container for prompting, the container comprising a projection formed in the container bottom, wherein the light is coupled into the container at the projection, and the container comprising scattering centers configured to scatter the light coupled in,
when said computer program is run by a computer.

31. A non-transitory digital storage medium having a computer program stored thereon to perform the method of operating a system for monitoring liquid intake of a user, said method comprising:
connecting a container comprising a projection or a curvature on a bearing surface, said projection or curvature being formed as a part of the container bottom, so that stability of the container is reduced when the container is placed down onto the bearing surface, to a socket configured to receive the container, so that the container can be placed down in a stable manner in connection with the socket;
determining an amount of liquid removed from the container by means of a monitor; and
prompting the user, as a function of the amount of liquid removed, by means of a prompter, wherein the monitor and the prompter are arranged within the socket,
when said computer program is run by a computer.

* * * * *